(12) United States Patent
Zhou

(10) Patent No.: US 10,106,853 B2
(45) Date of Patent: Oct. 23, 2018

(54) CUL4B AS PREDICTIVE BIOMARKER FOR CANCER TREATMENT

(71) Applicant: CORNELL UNIVERSITY, Ithaca, NY (US)

(72) Inventor: Pengbo Zhou, Princeton Junction, NJ (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/398,870

(22) PCT Filed: May 3, 2013

(86) PCT No.: PCT/US2013/039433
§ 371 (c)(1),
(2) Date: Nov. 4, 2014

(87) PCT Pub. No.: WO2013/166366
PCT Pub. Date: Nov. 7, 2013

(65) Prior Publication Data
US 2015/0119446 A1    Apr. 30, 2015

Related U.S. Application Data

(60) Provisional application No. 61/679,960, filed on Aug. 6, 2012, provisional application No. 61/642,744, filed on May 4, 2012.

(51) Int. Cl.
| | |
|---|---|
| *C12N 15/113* | (2010.01) |
| *C12Q 1/6886* | (2018.01) |
| *G01N 33/574* | (2006.01) |
| *A61K 31/4745* | (2006.01) |
| *A61K 31/496* | (2006.01) |
| *A61K 31/7105* | (2006.01) |

(52) U.S. Cl.
CPC ........ *C12Q 1/6886* (2013.01); *A61K 31/4745* (2013.01); *A61K 31/496* (2013.01); *A61K 31/7105* (2013.01); *C12N 15/113* (2013.01); *G01N 33/57407* (2013.01); *G01N 33/57484* (2013.01); *C12N 2310/14* (2013.01); *C12N 2320/31* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

2007/0154915 A1* 7/2007 Inazawa ............... C12Q 1/6886
435/6.12
2008/0312093 A1  12/2008 Inazawa et al.

OTHER PUBLICATIONS

MedlinePlus (www.nlm.nih.gov/medlineplus/colorectalcancer.html, retrieved Jan. 25, 2016).*
Braun M.S. et al., "Predictive Biomarkers of Chemotherapy Efficacy in Colorectal Cancer: Results from the UK MRC FOCUS Trial", Journal of Clinical Oncology 26(16):2690-2698 (10 pages total) (Jun. 1, 2008).
Desai S.D. et al., "Transcription-Dependent Degradation of Topoisomerase I-DNA Covalent Complexes", Molecular and Cellular Biology 23(7):2341-2350 (Apr. 2003).
Desai S.D. et al., "Ubiquitin/26S Proteasome-Mediated Degradation of Topoisomerase I as a Resistance Mechanism to Camptothecin in Tumor Cells", Cancer Research 61:5926-5932 (Aug. 1, 2001).
Gilbert DC et al., "Topoisomerase I Inhibition in Colorectal Cancer: Biomarkers and Therapeutic Targets", British Journal of Cancer 106(1):18-24 (2012).
Kerzendorfer C. et al., "Mutations in Cullin 4B Result in a Human Syndrome Associated With Increased Camptothecin-Induced Topoisomerase I-Dependent DNA Breaks", Human Molecular Genetics 19(7):1324-1334 (2010).
Lee J. et al., "DCAFs, the Missing Link of the CUL4-DDB1 Ubiquitin Ligase", Molecular Cell 26:775-780 (Jun. 22, 2007).
Paddison P.J. et al., "Short Hairpin RNAs (shRNAs) Induce Sequence-Specific Silencing in Mammalian Cells", Genes & Development 16:948-958 (2002).
Pommier Y., "Topoisomerase I Inhibitors: Camptothecins and Beyond", Nature Reviews—Cancer 6:789-802 (Oct. 2006).
Database; GenBank, AK 305687, (2 pages total) (Aug. 20, 2011).
International Search Report dated Aug. 29, 2013 received from related Application No. PCT/US2013/039433.

* cited by examiner

*Primary Examiner* — J. E. Angell
(74) *Attorney, Agent, or Firm* — Scully, Scott, Murphy & Presser, P.C.

(57) ABSTRACT

The current disclosure describes materials and methods for identifying subjects that would benefit from treatment with a DNA topoisomerase 1 inhibitor, based on the levels of cullin 4B gene, RNA and protein levels in the subject. The disclosure identifies CUL4B as a predictive biomarker for cancer diagnosis and the subsequent treatment with directed therapeutic agents. The current disclosure also identifies novel therapeutic agents that modulate the level of CUL4B expression, and sensitize a subject to treatment with a second therapeutic agent.

Figure 1A:
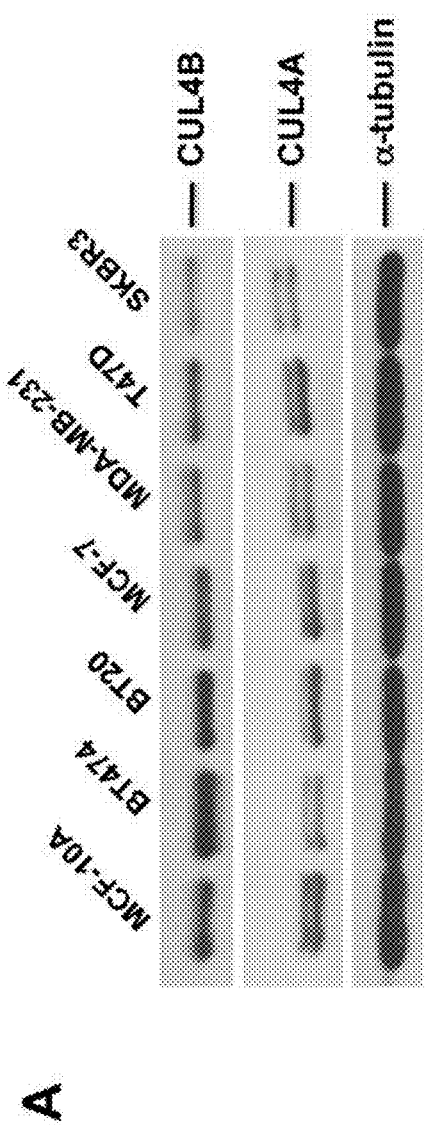

14 Claims, 17 Drawing Sheets
(7 of 17 Drawing Sheet(s) Filed in Color)
Specification includes a Sequence Listing.

A

B

E

F

CUL4B AS PREDICTIVE BIOMARKER FOR CANCER TREATMENT

CROSS REFERENCE TO RELATED APPLICATIONS

This application claims priority from U.S. Provisional Application No. 61/642,744, filed May 4, 2012, and U.S. Provisional Application No. 61/679,960, filed Aug. 6, 2012, the entire contents of both of which are incorporated herein by reference.

STATEMENT REGARDING FEDERALLY SPONSORED RESEARCH

This invention was made with government support under grant number 5R01 CA098210 awarded by the National Institutes of Health. The government has certain rights in the disclosure.

INCORPORATION BY REFERENCE OF SEQUENCE LISTING

The Sequence Listing in an ASCII text file, named 28770_5925_04_US_SequenceListing.txt of 17 KB, created on Nov. 3, 2014, and submitted to the United States Patent and Trademark Office via EFS-Web, is incorporated herein by reference.

FIELD OF THE DISCLOSURE

The present disclosure relates to compositions and methods concerning the identification, treatment and characterization of cancer, as well as the use of novel biomarkers for therapeutic, prognostic, and diagnostic applications, particularly those methods and compositions related to assessing and/or identifying cancer, directly or indirectly related to Cullin 4B (CUL4B) and DNA topoisomerase 1 (Top1) activity and/or expression.

BACKGROUND OF THE DISCLOSURE

Predictive biomarkers correlate with the impact of certain cancer treatments and thus, patient outcome. Accurate predictive biomarkers are difficult to obtain as many variables exist that may affect the validity of a marker, including but not limited to, downstream or upstream effectors of the biomarker, transcriptional regulators, and/or DNA modification.

The supercoiled nature of DNA requires topological modification during transcription, replication and DNA repair. (See, Gilbert, D C., et al., *Cancer Research UK* (2012) 106:18-24). These modifications are commonly carried out by DNA topoisomerases that that cleave the sugar-phosphate backbone of DNA without altering its chemical composition. Top1 is ubiquitously expressed and plays key roles in DNA replication, transcription, recombination and repair, primarily functioning to break a single strand of double-stranded, supercoiled DNA which enables the DNA to relax before it is re-ligated. (See, Wang, J C. *J. Mol Biol* (1971) 55:523-533). Top1 is overexpressed in many types of tumors making it the target of many anti-tumor, chemotherapeutic agents (See, Gilbert, D C., et al. (2012)).

The antitumor activity of camptothecin(s) (CPT), a known DNA topoisomerase 1-directed anti-cancer agent, is attributed to CPTs ability to bind TOP1 and inhibit the re-ligation step of the breakage/re-annealing reaction of DNA during the cell-cycle. CPTs covalently trap TOP1-DNA intermediates, resulting in accumulation of a reversible Top1-CPT-DNA covalent complex, often referred to as the cleavable complex (TOP1 ccs) (See, e.g., Zhang, H-F, et al., *Cancer Research* (2004) 64:1114-1121). The Top1 cleavable complex acts as a road block, colliding with moving replication forks or the RNA polymerase elongation complexes, thereby facilitating the conversion of single strand DNA breaks into the lethal DNA double stranded breaks (See, Chen, A Y., *Annu. Rev. Pharmacol. Toxicol.* (1994) 34:191-218). Following CPT treatment, Top1 is rapidly degraded by the ubiquitin-proteasome pathway, which is believed to be a critical mechanism to control the cellular response to the repair of CPT-induced DNA lesions and promote resistance to CPT cytotoxicity.

Ubiquitin-dependent proteolysis is carried out by the sequential action of three enzymes, the E1 ubiquitin-activating enzyme, the E2 ubiquitin-conjugating enzyme, and the E3 ubiquitin ligase among which the E3 ubiquitin ligase binds directly to the target protein and thus is exclusively responsible for conferring substrate specificity (See, Hershko, A., *J. Biol. Chem.* (1983) 258:8206-8214). The cullin family of proteins are the major components of the E3 ubiquitin ligase complex, generally functioning as scaffold proteins binding RING-finger proteins (See, Zhang, H-F, et al., (2004)). In mammalian cells there are two distinct Cullin 4 genes, CUL4A and CUL4B that share 82% sequence identity and overlapping functions. Distinct activities of the two CUL4s have also been reported, resulting from their differential expression during male meiosis and from their preferential subcellular distribution (predominantly cytoplasm for CUL4A and nuclear for CUL4B). CUL4B has a unique N-terminal extension that enables the protein's ability to bind unique adaptors (e.g. Aryl hydrocarbon receptor) and assemble a CUL4B-specific E3 ligase complex. To date, the degree of functional redundancy and difference between CUL4A and CUL4B, and the specific targets of CUL4A or CUL4B are not fully understood.

SUMMARY OF THE DISCLOSURE

The current disclosure reveals that cancer cells with elevated levels of CUL4B expression are resistant to treatment with Top1-directed chemotherapeutic compounds such as camptothecin and as such, an analysis of CUL4B expression is useful to identify subjects that will be either resistant or responsive to treatment with a Top1-directed chemotherapeutic agent. Therefore, methods disclosed herein include, for example, measuring CUL4B expression in a biological sample obtained from a mammalian subject with cancer and identifying the level of CUL4B expression in the sample, wherein an elevated level of CUL4B expression in the sample identifies the subject as a subject that will be resistant to treatment with a Top1-directed chemotherapeutic agent. Conversely, wherein if the level of CUL4B expression is reduced when compared to a control, or the level of CUL4B expression is equal to the levels exhibited by control samples or data sets, the subject will be identified as a subject that will be responsive or sensitive to treatment with a Top1-directed chemotherapeutic agent.

In some embodiments of the present disclosure, the level of CUL4B expression is measured based on detecting CUL4B genomic copy number, detecting the level of CUL4B mRNA, or detecting the level of CUL4B protein or fragments thereof. The level of CUL4B expression can be determined by a variety of methods and processes, including but not limited to, RT-PCR, real-time quantitative PCR, Next-Generation (Next-Gen) Sequencing (NGS), Southern blotting, Northern blotting, immunohistochemistry, immunofluorescent assay, Western blotting, or ELISA.

In certain aspects of the current disclosure, the level of CUL4B expression in the sample is compared to a control level.

Another aspect of the current disclosure describes a method of treating cancer in a subject who has been identified as expressing an elevated level of CUL4B, based on administering to the subject an effective amount of an agent that inhibits expression or activity of CUL4B, and a Top1-directed chemotherapeutic compound, wherein inhibition of expression of CUL4B sensitizes the cancer to the Top1-directed chemotherapeutic compound.

In certain aspects of the current disclosure, the agent that inhibits the expression or activity of CUL4B is selected from a nucleic acid, an antibody, or a small molecule compound that directly targets CUL4B, more specifically an siRNA or shRNA. In yet another aspect, the current disclosure describes an isolated nucleic acid agent characterized by [SEQ ID NO. 1] or [SEQ ID NO. 2], which agent reduces CUL4B expression.

These and other embodiments of the disclosure will be readily apparent to those of ordinary skill in view of the disclosure herein.

BRIEF DESCRIPTION OF DRAWINGS AND TABLES

The patent or application file contains at least one drawing executed in color. Copies of this paper or patent application publication with color drawing(s) will be provided by the Office upon request and payment of the necessary fee.

FIG. 1. CPT-induced TOP1 degradation in breast cancer cell lines. A) Expression of endogenous CUL4A and 4B in breast cancer cell lines. Total cell lysates were prepared from the indicated breast cancer cell lines and subjected to SDS PAGE and immunoblotting with antibodies against CUL4A, 4B and α-tubulin. The non-cancerous MCF-10A cell line was used as a control for comparison. B) CPT-induced TOP1 degradation in breast cancer cell lines. Cells were treated with 12.5 μM CPT or 1% DMSO for 4 hours, replenished with CPT-free fresh medium and incubated at 37° C. for 30 minutes to reverse the formation of TOP1 cleavable complex. Cells were then lysed and immunoblotted with the TOP1 and α-tubulin antibodies.

FIG. 2. CUL4B interacted with Top1 and induced Top1 degradation in the presence of CPT. A) Knockdown of CUL4B impaired CPT-induced Top1 degradation. BT474 cells were infected with lentiviral shCUL4B, shCUL4A or control non-targeting shRNA, and selected for stable CUL4B$^{k/d}$ or CUL4A$^{k/d}$ cells upon treatment with puromycin. Following treatment with CPT (50 μM) for 1 hour, cells were replenished with CPT-free fresh medium and incubated at 37° C. for 30 minutes. Top1 degradation was assessed by immunoblotting with an anti-Top1 antibody. Levels of α-tubulin were measured as a loading control. B) Association of CUL4B with Top1 following CPT treatment. BT474 cells were treated with proteosome inhibitor MG132 (15 μM) for 3 hours, and were subjected to crosslinking with 0.2 mM Dithiobis[succinimidyl propionate](DSP) for the last 30 min at room temperature. Cell lysates were prepared, and immunoprecipitated with the anti-Top1 or anti-CUL4B antibodies, and then immunoblotted using antibodies against CUL4B or Top1, respectively. IgG immunoprecipitates served as the negative control. C) Knockdown of CUL4B using a second shCUL4B-2 impaired CPT-induced Top1 degradation. BT474 cells were infected with lentiviral shCUL4B-2, shCUL4A-2 or control non-targeting shRNA and selected for stable CUL4B$^{k/d}$ or CUL4A$^{k/d}$ cells upon treatment with puromycin. Following treatment with CPT (50 μM) for 1.5 hr, cells were replenished with CPT-free fresh medium and incubated at 37° C. for 30 min. Top1 degradation was assessed by immunoblotting with the anti-Top1 antibody. Levels of α-tubulin were measured as a loading control. D) CUL4B inactivation sensitized BT474 cells to cytotoxic killing by camptothecin. BT474, BT474-CUL4A$^{k/d}$ or BT474-CUL4B$^{k/d}$ cells were synchronized with 1 μM nocodazole for 13 hours released in fresh medium, treated with the indicated concentrations of CPT for three days, and subjected to the XTT assay to measure the cytotoxic responses to CPT. These data represent the mean value of cell survival ratio. The bars indicate the S.E. of six independent experiments. Statistical significance in cellular response to CPT between control BT474 cells and CUL4A$^{k/d}$ or CUL4B$^{k/d}$ cells were assessed by a two-tailed unpaired student t-test (***: p<0.001). The same results were obtained with a second lentiviral shRNA for CUL4A and CUL4B, as well as in T47D breast cancer cells. E, F) Knockdown of CUL4B increased the sensitivity of T47D cells to camptothecin. T47D cells were synchronized with 100 nM paclitaxel for 36 hr and then released in fresh medium with the indicated concentrations of CPT for three days, and subjected to XTT assay to measure the cytotoxic responses to camptothecin. The data represent the mean value of cell survival ratio, and the bars indicate the S.E. of six independent experiments. Statistical significance in cellular response to camptothecin between control cells and CUL4A$^{k/d}$ or CUL4B$^{k/d}$ BT474 cells are assessed by student's t-test.

FIG. 3. CUL4B$^{k/d}$ BT474 cells are susceptible to CPT-induced DNA damage. A) Persistent DNA damage in CPT-treated BT474-CUL4B$^{k/d}$ cells. Control or CUL4B$^{k/d}$ BT474 cells were treated with 2 μM of CPT for the indicated time periods, replenished with CPT-free fresh medium, incubated at 37° C. for 1 hour to repair DNA damage, and subjected to immunoblotting with the anti-γH2AX antibody to determine the extent of DNA damage. B) Immunofluorescent detection of γH2AX foci in control or CUL4B$^{k/d}$ BT474 cells following CPT treatment. BT474 cells were infected with lentiviral control shRNA (shCtrl) or shCUL4B, treated with 2 μM CPT for 2 hours and replenished with CPT-free fresh medium, incubated at 37° C. for 1 hour to repair DNA damage. γH2AX foci were detected by immunofluorescent assay with the rabbit anti-γH2AX antibody and goat anti-rabbit secondary antibody conjugated with cy3 (red). Nuclei were stained with DAPI (blue). C, D) Percentage of γH2AX-positive cells and number of persistent γH2AX foci in a total of 300 γH2AX-positive cells. All values were presented as mean±S.E. Statistical significance was assessed by a two-tailed unpaired Student t-test (***: p<0.001). E, F) The inactivation of CUL4B attenuated the Mre11-Chk1 DNA damage checkpoint revealed by the reduced phosphorylation of Mre11 and chk1.

Figure 4A:
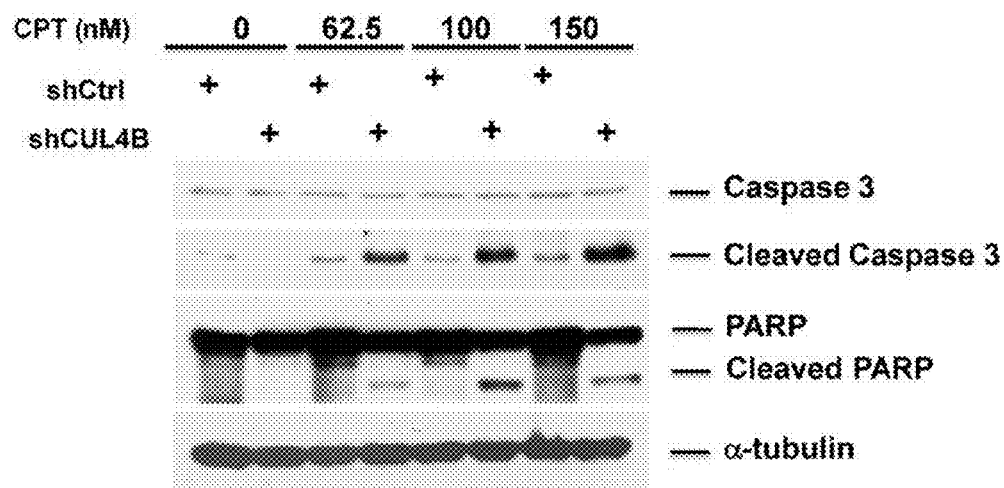
Figure 4B:
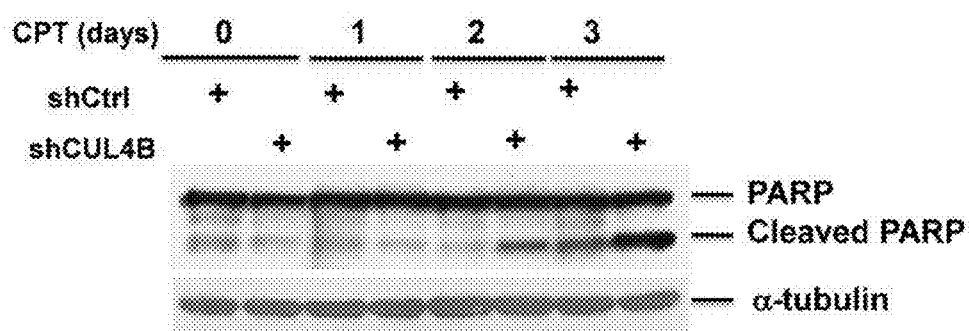
Figure 4C:
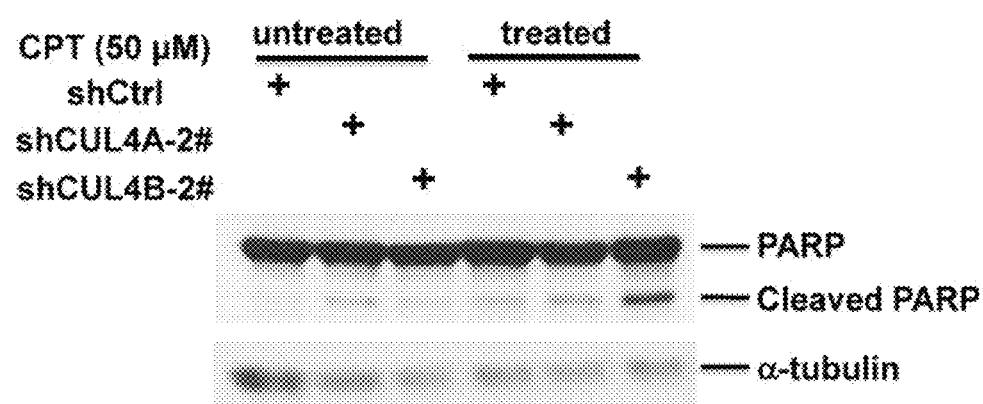

FIG. 4. Marked enhancement of apoptosis in BT474-CUL4B$^{k/d}$ cells following CPT treatment. A, B) Control (shCtrl) or CUL4B$^{k/d}$ BT474 (shCUL4B) cells were treated with indicated concentrations of CPT for 72 hours (A) or 100 nM CPT for 1, 2 and 3 days (B). Cells were then lysed and immunoblotted with antibodies against native or cleaved caspase 3 or PARP to measure the induction of apoptosis. C) Control, CUL4A$^{k/d}$ and CUL4B$^{k/d}$ BT474 cells were treated with 100 nM CPT for 3 days. Cell lysates were prepared and immunoblotted with antibodies against native or cleaved PARP.

FIG. 5. CUL4B inactivation sensitized BT474 xenograft tumors to topotecan. Stable TGL-BT474 cells (BT474 cells stably expressing GFP-luciferase reporter) were established by retroviral transduction and FACS sorting. The resulting TGL-BT474 cells were infected with recombinant lentiviruses expressing non-targeting shCtrl, shCUL4A or shCUL4B, followed by selection of infected cells with 4 µg/ml puromycine for one week. A) Knockdown of endogenous CUL4A and 4B were verified by immunoblotting. B, C) $1 \times 10^7$ of control, CUL4A$^{k/d}$, or CUL4B$^{k/d}$ TGL-BT474 cells were injected subcutaneously in the right flank of each athymic Nu/J nude mice, treated (i.p.) with toptoecan at a dose of 5 mg/g on every 4$^{th}$ day, and tumor burden was measure by bioluminescent imaging. Statistical significance in tumor burden between control and CUL4A$^{k/d}$ or CUL4B$^{k/d}$ xenograph are assessed by a two-tailed unpaired student t-test (***: $p<0.001$). D) Growth rate of control, CUL4A$^{k/d}$ and CUL4B$^{k/d}$ BT474 cells in vitro. The same number of control, CUL4A$^{k/d}$ and CUL4B$^{k/d}$ BT474 cells were seeded to 96-well plates and cell proliferation was measured using the XTT Cell Proliferation Assay Kit. The data represent the mean value of fold change of cells. Bars indicate the S.E. of six independent experiments. Statistical significance in cellular rate between control cells and CUL4A$^{k/d}$ or CUL4B$^{k/d}$ cells are assessed by student's t-test. E-F) Growth rate of control, CUL4A$^{k/d}$ and CUL4B$^{k/d}$ TGL-BT474 xenograft in vivo. $1 \times 10^7$ of control, CUL4A$^{k/d}$ or CUL4B$^{k/d}$ TGL-BT474 cells were injected subcutaneously in the right flank of each mouse of athymic Nu/J nude mice, and tumor burden was measured by bioluminescent imaging (E). On the 22$^{nd}$ day, tumors were collected, and the weight of exercised tumors was measured after mice were sacrificed (F).

Figure 6:
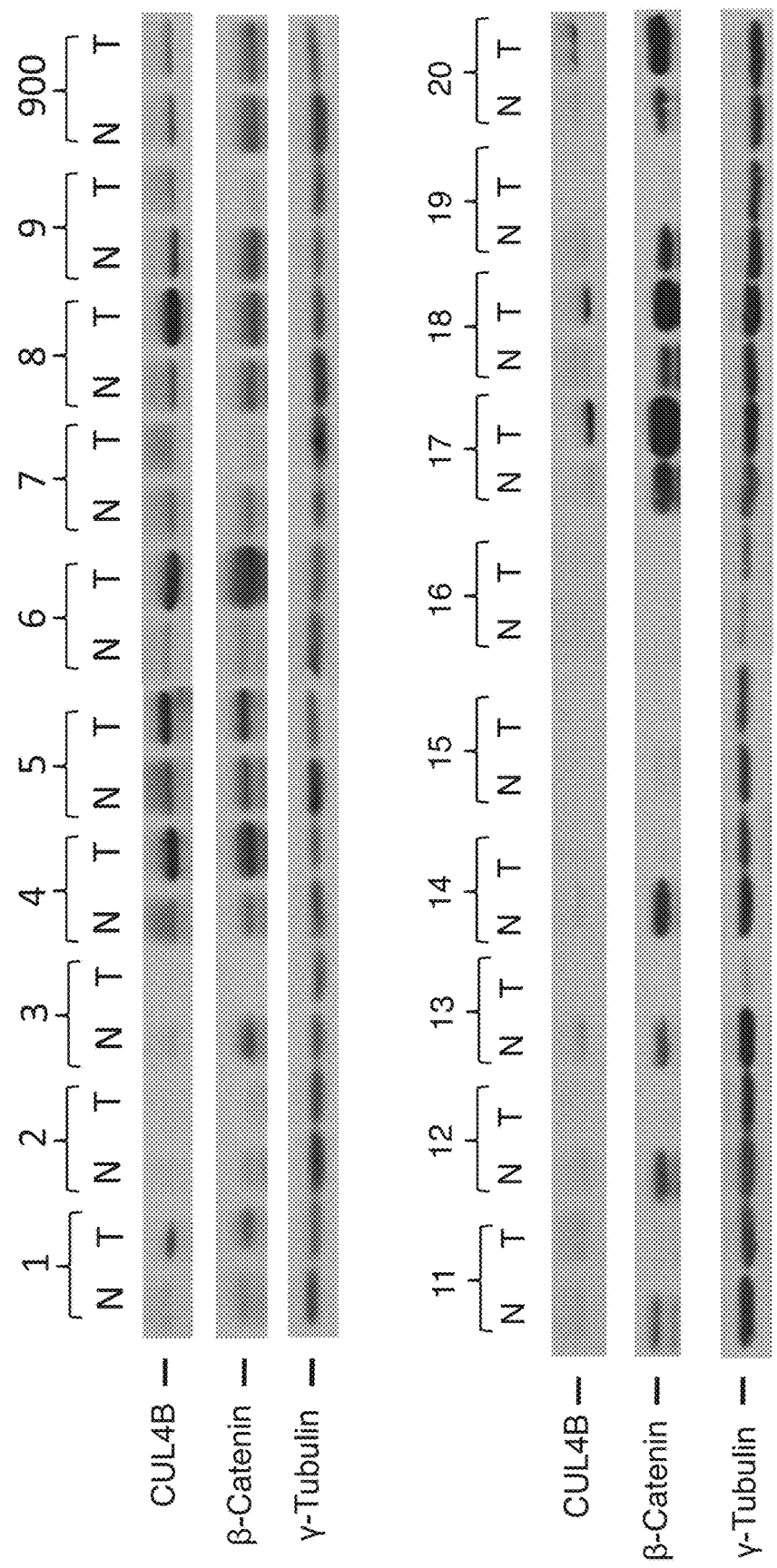

FIG. 6. CUL4B expression is elevated in human colon cancer samples. Twenty colon cancer specimens (columns) were obtained as surgical specimens, frozen and proteins were extracted and analyzed using SDS-PAGE and Western blotting with the anti-CUL4B antibody (2$^{nd}$ row) using γ-tubulin as a control (4$^{th}$ row) CUL4B protein expression levels in tumors (T) were compared to that of non-cancerous (N) control tissue (surgical margins, benign samples) samples obtained from each subject. Western blotting revealed that CUL4B expression was elevated in 45% (9 of 20 samples) of the samples analyzed when compared to that of the non-cancerous control for each patient sample.

Figure 7A:
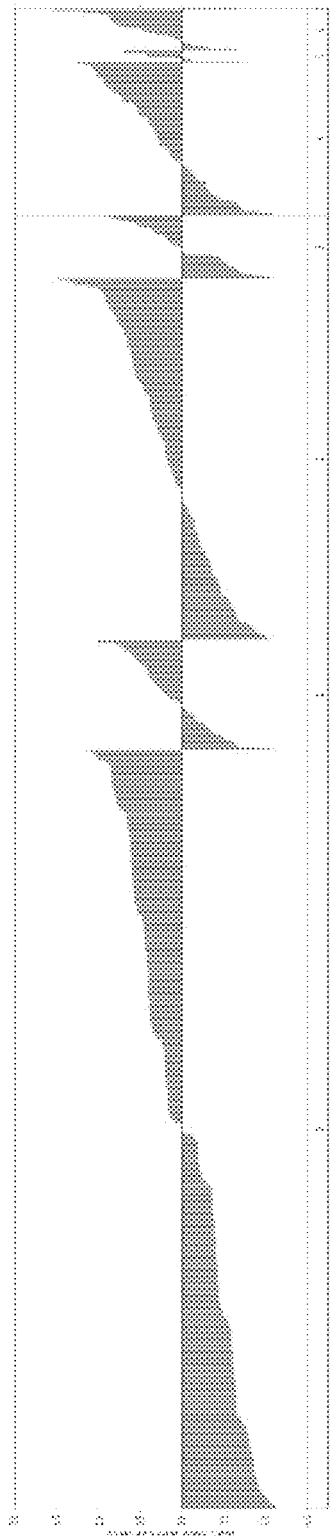
Figure 7B:
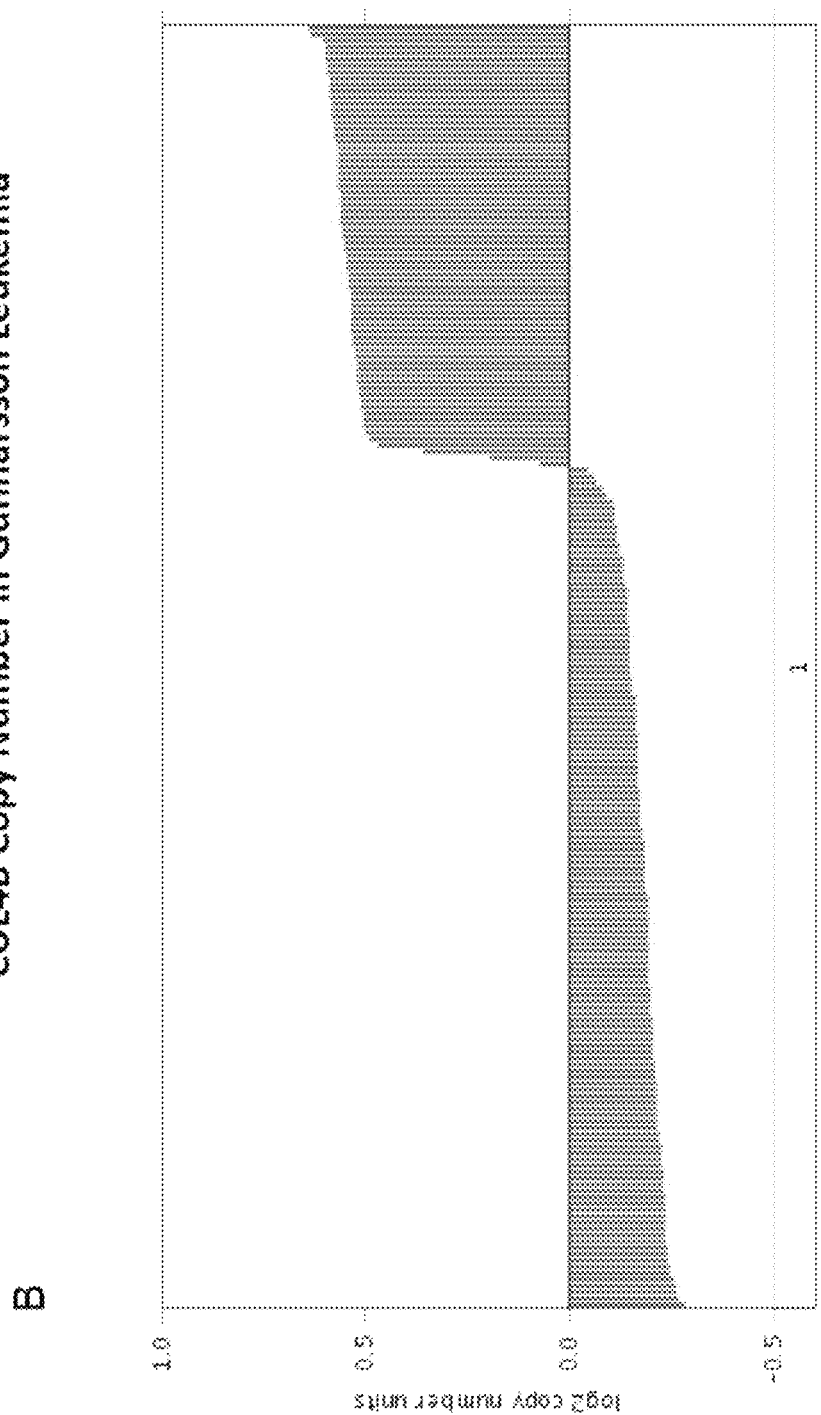
Figure 8A:
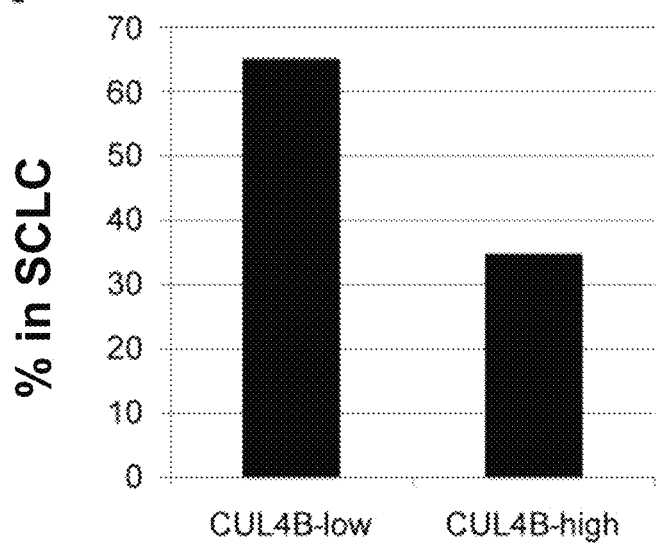
Figure 8B:
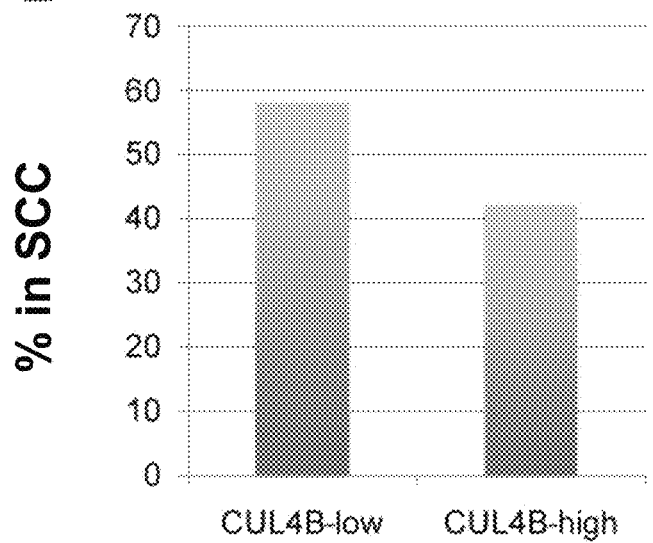

FIG. 7. CUL4B is amplified in Chronic Lymphocytic Leukemia. A) CUL4B is amplified in colorectal cancers. Genomic DNA was extracted from a total of 881 colorectal cancer specimens for high density SNP array analysis of CUL4B gene copy number. CUL4B gene amplification was observed in 37 out of 65 cases of cecum adenocarcinomas (57%), 122 out 212 cases of colon adenocarcinomas (57.5%), 19 out of 37 cases of colon mucinious adenocarcinomas (51.4%), 5 out of 7 cases of rectal adenocarcinomas (71.4%), 19 out of 24 cases of rectosigmoid adenocarcinomas (79.2%), Note that there was only one case of Rectosigmoid mucinious adenocarcinomas. B) Genomic DNA was extracted from a total of 203 chronic leuphocytic leukemia specimens for high density SNP array analysis of the CUL4B gene copy number. CUL4B gene amplification was observed 70 out of 203 cases of Chronic Lymphocytic Leukemia (34.5%), FIG. 8. CUL4B is overexpressed in a subset of small cell and squamous cell lung carcinomas. Tissue microarrays were generated from 72 cases of small cell lung carcinoma specimens (A) and 112 cases of squamous cell lung carcinomas (B). CUL4B protein levels were determined by immunohistochemistry with the anti-CUL4B antibody, and quantified by the H Score method. An H score of 150 or above is considered high CUL4B expression. SCLC, small cell lung carcinomas; SCC, squamous cell carcinomas.

Table 1. Elevated CUL4B expression in cancer via gene amplification. This table shows various types of cancer samples (Left Column) for which CUL4B gene expression was elevated, as well as the percentage of each cancer type that overexpressed CUL4B.

DETAILED DESCRIPTION OF THE DISCLOSURE

The current disclosure reveals that CUL4B is a predictive biomarker for a cancer patient's responsiveness to topoisomerase 1 (Top1)-directed therapeutic agents. When expression levels of CUL4B are elevated in a subject, the subject will be resistant to treatment with a DNA topoisomerase 1 (Top1)-directed therapeutic agent. As described herein, CUL4B is overexpressed in several types of cancer, including but not limited to, breast, colorectal and lung carcinomas. It has been demonstrated herein using cancerous cells, tissue samples and xenograft tumor models overexpressing CUL4B that aberrant expression of CUL4B at elevated levels is associated with resistance to Top1-directed chemotherapeutic agents, such as camptothecin, due to a direct interaction between CUL4B and Top1 resulting in the ubiquitination and subsequent degradation of Top1, a mechanism that results in limited efficacy of Top1-directed drugs by reducing the abundance of the Top1 target in a subject. Moreover, the data described herein reveal that inhibition of CUL4B reduced Top1 degradation, and activation of the MRE11 and Chk1-dependent DNA damage checkpoint, increasing apoptosis-mediated cell death as evidenced by elevated PARP and cleaved-caspase 3 expression levels, thus sensitizing a cell or organism to Top1-directed therapeutic agents. Taken together, the level of CUL4B expression can be used to classify a subject according to their likelihood of responding to treatment with a Top1-targeting agent. This classification is a useful means of directing personalized treatment to cancer patients having elevated CUL4B expression with a CUL4B inhibitor in combination with a TOP1 therapeutic agent.

Terminology

The term "increase," "elevated" or "elevate" means that the amount of an entity identified (such as CUL4B expression or CUL4B activity), measured or analyzed in a test sample is higher relative to a control. Non-limiting examples, include but are not limited to, a 2-5%, 5-10%, 10-15% 10-20% increase over a control, or at least 10%, 20%, 30%, 40%, 50%, 60%, 70%, 80%, 90%, 100%, 200% or greater increase over a control, or at least 1 fold, 1.5 fold, 2 fold, 3 fold or greater, increase relative to a control.

The term "decrease" or "reduction" means the entity identified, measured or analyzed in a test sample is less than a control. Non-limiting examples, include but are not limited to, 10-20% decrease over a control value, or at least, a 2-5%, 5-10%, 10-15% 10-20% decrease when compared to a control, or at least 10%, 20%, 30%, 40%, 50%, 60%, 70%, 80%, 90%, 100%, 200% or greater decrease relative to a control, or at least 1 fold, 1.5 fold, 2 fold, 3 fold or greater, decrease relative to a control.

The term "level" as used herein shall mean the amount of an entity present. Non-limiting examples of the level of an entity of the current disclosure include the amount of protein, RNA, DNA, gene copies present in a cell. In an aspect of the current disclosure the amount of CUL4B protein, DNA or RNA is the level of CUL4B in a cell, biological sample or subject.

An "elevated level of CUL4B expression" as used in the current disclosure shall mean an increase in the amount of CUL4B protein, RNA (e.g., mRNA), or gene copies present in a cell, organism or sample.

The term "CUL4B gene" or "cullin 4B gene" as referred to in the current disclosure is a member of the cullin gene family also known as MRXS15, SFM2, MRXSC, MRXHF2, located on the X-chromosome (Xq23) spanning nucleotides 119658444-119709684 comprising 51240 base pairs. As used herein, the term "CUL4B gene" includes the nucleic acid molecule represented by RefSeq ID No: NG_009388, as well as allelic variants thereof.

The CUL4B gene produces multiple CUL4B mRNA transcripts, including NM_003588.3 and NM_001079872.1, which translate into multiple CUL4B protein isoforms of NP_003579.3 (913 amino acids) [SEQ ID NO: 3] and NP_001073341.1 (895 amino acids) [SEQ ID NO: 8], respectively. The two isoforms differ only in their N-terminus, with the shorter isoform lacking 15 contiguous amino acids in the longer isoform. As used herein, the term "CUL4B mRNA" refers to NM_003588.3, NM_001079872.1, as well as allelic variants of the reported sequences of NM_003588.3 and NM_001079872.1. The term "CUL4B protein" refers to SEQ ID NO: 3, SEQ ID NO: 9, as well as allelic variants thereof.

The term "allelic variant" as used herein refers to variants having one or more alterations in the sequence of a gene, transcript or protein which naturally occur in a population. An allelic variant may share a sequence identity of at least 90%, 95%, 98%, 99%, or greater to a reported or specified nucleotide or protein sequence.

The phrase "CUL4B activity" or "CUL4B function" refers to the ability of CUL4B to bind other subunits of the CUL4B E3 ligase complex, such as DDB1, Rbx1 or DCAF substrate receptors (DDB1, CUL4 associated factors), regulators, effectors (e.g. substrates), respond to changes in cellular conditions, or regulate cellular homeostasis. A non-limiting example of CUL4B activity is the ability of CUL4B to bind Top1 or the Top1-DNA complex.

The term "topoisomerase 1," "DNA topoisomerase 1" or "Top1" refers to the polypeptide encoded by the nucleic acid corresponding to GenBank Accession No: BC136297.1 or GL223460079, and the human Top1 polypeptide corresponds to the protein sequence set forth in RefSeq ID No: NM_003286 or NP_003277.1 and variants such as allelic variants thereof, including NM_003286.2. Topoisomerase1 is referred in the art as TOPI or TOP1. DNA topoisomerase is an enzyme that controls and alters the topologic states of DNA during transcription, and catalyzes the transient breaking and rejoining of a single strand of DNA which allows the strands to pass through one another, thus altering the topology of DNA. The gene for Top1 is located within chromosome 20 and has pseudogenes which reside within chromosomes 1 and 22. The activity of Top1 refers to the polypeptides enzymatic activity to catalyze the transient breaking and rejoining of a single strand of DNA, where one strand pass through one another, thus altering the topology of DNA.

The term "Top1 inhibitor" or "Top1-directed therapeutic agent" or "Top1-directed therapeutic compound" as used in the current disclosure refers to any entity which mediates some, all or part of the biological function, activity or level of Top1 by acting directly or indirectly on the gene, gene product or polynucleotide of Top1. Top1-directed therapeutic agents can directly or indirectly inactivate Top1. In some embodiments, Top1-directed therapeutic compounds act directly on Top1, for example, on the Top1 protein (through, e.g., binding to the Top1 protein or to a Top1-DNA complex) to inactivate the activity of the Top1 protein. Such direct Top1-directed therapeutic agent include small molecule compounds, for example, camptothecin (CPT) and analogues thereof, including but not limited to, irinotecan and topotecan, and derivatives thereof, as well as agents that mimic the therapeutic activity of CPT. Top1-directed therapeutic agents will also include pEGylated or nanoparticle-bearing derivatives of Top1 inhibitors, as well as Top1 inhibitors attached to tumor-targeting antibodies, including but not limited to PEG-SN-38 and Labetuzumab-SN-38, respectively.

The term "sensitize," or the phrase "increase sensitivity or responsiveness to" a therapeutic agent, as used in the current disclosure, refers to the ability of a treatment disclosed herein to result in an improved effectiveness of the therapeutic agent (e.g., in killing or preventing the growth of cancerous cells) in the subject. For example, providing a cell or subject with an effective amount of an agent that reduces the level of CUL4B sensitizes a cell, previously resistant, to treatment with a Top1-directed chemotherapeutic agent.

The term "resistant" to a therapeutic agent means that the therapeutic agent fails to achieve the intended therapeutic effects (e.g., killing or preventing the growth of cancerous cells) in the subject being treated. For example, as shown herein, cancerous cells having elevated levels of CUL4B expression are resistant to CPT (a Top1-directed chemotherapeutic agent).

The term "responsive" as used in the current disclosure means a desired reaction of a cell, organism or subject to treatment with a therapeutic agent, such as a Top1-directed therapeutic agent or CUL4B inhibitor.

The term "entity" refers to any structural molecule or combination of molecules.

The term "agent" is employed herein to refer to any kind of compound, molecule or ion and any combination thereof. In one embodiment of the disclosure the agent is a small molecule. In another embodiment of the disclosure, the agent is a biological molecule, including, but not limited to, a protein or a peptide or a nucleic acid, or an ion. In another embodiment, the nucleic acid is an interfering RNA. In yet another embodiment, the agent is an antibody or fragment thereof.

The term "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

In the context of this disclosure, the term "small molecule" refers to small organic compounds, including but not limited to, heterocycles, peptides, saccharides, steroids, antibodies and the like. The small molecule modulators can have a molecular weight of less than about 1500 Daltons, 1200 Daltons, 1000 Daltons, or 800 Daltons. In some embodiments, a small molecule modulator is less than 500 Daltons. The small molecules can be modified to enhance efficacy, stability, pharmaceutical compatibility, and the like. Candidate modulator compounds from libraries of synthetic or natural compounds can be screened. Synthetic compound libraries are commercially available from a number of companies including Maybridge Chemical Co. (Trevillet, Cornwall, UK), Comgenex (Princeton, N. J.), Brandon Associates (Merrimack, N.H.), Microsource (New Milford, Conn.), and ChemBridge (San Diego, Calif.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds may be further modified through conventional chemical and biochemical techniques.

The term "peptide" refers to a linear series of amino acid residues linked to one another by peptide bonds between the alpha-amino and carboxyl groups of adjacent amino acid residues.

The term "synthetic peptide" is intended to refer to a chemically derived chain of amino acid residues linked together by peptide bonds. The term synthetic peptide is also intended to refer to recombinantly produced peptides in accordance with the present disclosure.

The phrase "subject in need thereof" as used herein refers to any mammalian subject in need of a treatment, particularly cancer subjects, including cancer subjects exhibiting elevated levels CUL4B expression. The methods of the current disclosure can be practiced on any mammalian subject that has a risk of developing cancer. Particularly, the methods described herein are most useful when practiced on humans.

A "biological sample," "sample" or "samples" to be used in the disclosure can be obtained in any manner known to a skilled artisan. Samples can be derived from any part of the subject, including whole blood, tissue, lymph node or a combination thereof. Conversely, a "control sample" is typically a sample which does not contain cancerous cells (e.g., a sample from benign tissues), or a sample which does not exhibit elevated CUL4B levels or activity (including samples from benign or cancerous tissues, or histologically normal tissue adjacent but outside the margin of tumors). Non-limiting examples of control samples for use in the current disclosure include, non-cancerous tissue extracts, surgical margins extracted from the subject, isolated cells known to have normal CUL4B levels, obtained from the subject under examination or other healthy individuals. In one aspect, the control sample of the present disclosure is benign tissue. In one embodiment of the current disclosure, the amount of CUL4B in a sample is compared to either a standard amount of CUL4B present in a normal cell or a non-cancerous cell, or to the amount of CUL4B in a control sample. The comparison can be done by any method known to a skilled artisan.

As used herein, a "chemotherapeutic agent" is a chemical compound useful in the treatment of cancer. Examples of chemotherapeutic agents include: alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammall and calicheamicin omegall; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-di-azo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhône-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY 117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestanie, fadrozole, RIVISOR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rJL-2; LURTOTECAN® topoisomerase 1 inhibitor; ABARELLX® rmRH; and pharmaceutically acceptable salts, acids or derivatives of any of the above.

The term "binding", "to bind", "binds", "bound" or any derivation thereof refers to any stable, rather than transient, chemical bond between two or more molecules, including, but not limited to, covalent bonding, ionic bonding, and hydrogen bonding. Thus, this term also encompasses hybridization between two nucleic acid molecules among other types of chemical bonding between two or more molecules.

Herein, the term "substantially identical" when used in reference to nucleotide or protein sequences, refers to a nucleotide or protein sequence having an identity of at least 60%, 70%, 80%, 90%, 95%, 98% or greater to a specified nucleotide or protein sequence.

Methods of Identifying a Subject Resistant to Top1-Directed Chemotherapy.

The current disclosure reveals that cancer cells with elevated levels of CUL4B expression are resistant to treatment with Top1-directed chemotherapeutic agent such as camptothecin or topotecan. Therefore, this disclosure provides methods for identifying subjects that will likely be either resistant or responsive to treatment with a Top1-directed chemotherapeutic agent based on analysis of CUL4B expression. An elevated level of CUL4B expression in the subject identifies the subject as a subject that will likely be resistant to treatment with a Top1-directed chemotherapeutic agent. Conversely, wherein the level of CUL4B expression is lower than or equal to the levels exhibited by control samples or data sets, the subject will be identified as a subject that will likely be responsive or sensitive to treatment with a Top1-directed chemotherapeutic agent.

DNA exists as a double helix comprised of two intertwined DNA strands. During DNA replication or transcription these strands must be separated by helicase proteins in order to proceed. These processes are inherently constrained when the DNA chains coil around one other (supercoiling) a phenomenon that can only be addressed by breaking of a covalent bond in one of the two DNA strands. DNA topoisomerase 1 is an enzyme that cleaves a single DNA strand at the sugar-phosphate backbone facilitating the relief of torsional stress before re-annealing. Without this process torsional stress would continue to build in front of the transcriptional or replication machinery thus inhibiting the process. In order to reduce this stress, the Top1 enzyme creates transient breaks in the DNA and forms a covalently bonded cleavage complex with the cut DNA enabling the DNA to be uncoiled and resealed facilitating the proper performance of the transcriptional or replication machinery. Top1 is commonly overexpressed in cancer leading to increased transcription and DNA replication. Thus, Top1 is a target for many anti-cancer therapeutic agents.

A Top1-targeting therapeutic compound, such as a camptothecin, can bind to the Top1-DNA complex and prevents Top1 from properly functioning, resulting in toxic double-stranded DNA breaks and ultimate apoptosis of cancerous cells. CUL4B encodes a protein which forms a complex with adaptor molecules, including DDB1, DCAFs and Rbx1, or with aryl hydrocarbon receptor that functions as E3 ubiquitin ligases and catalyzes the polyubiquitination of specific protein substrates in the cell. Without limiting to any particular theory, it is believed that CUL4B E3 ligase plays a critical role in Top1 down-regulation through ubiquitination and degradation of a covalent complex formed among Top1, DNA and a Top1-targeting compound. It is believed that elevated levels of CUL4B E3 ligase lead to potentiated degradation and removal of the complex, resulting in essentially fewer Top1 molecules as target for the Top1-targeting compound and hence a reduced responsiveness of the cells to therapeutic effect of the compound.

A Top1-targeting chemotherapeutic agent useful in the methods disclosed herein is any agent that inhibits the biological activity of Top1, such as the protein activity of DNA topoisomerase. In another embodiment, a Top1 inhibitor is an agent commonly known by one of ordinary skill in the art that inhibits the gene expression and/or the biological activity of Top1, including the following non-limiting examples, antibodies, antibody fragments, small molecules, peptides, proteins, antisense nucleic acids, ribosomes, PNA, siRNA, oligonucleotides, aptamer, and peptide aptamer and derivatives and fragments thereof that inhibit Top1. Additionally, a Top1 chemotherapeutic agent useful in the methods of the present invention can be a nucleic acid-based inhibitor, nucleic acid construct, a peptide-based inhibitor or a small molecule inhibitor of Top1 or a polynucleotide encoding the same. In certain aspects, a nucleic-acid inhibitor may be an RNAi agent, for example a siRNA molecule or shRNA molecule. Exemplary Top1 chemotherapeutic agents are disclosed herein, and include but are not limited to CPT, or analogues thereof such as topotecan and irinotecan.

In other embodiments, a Top1-targeting chemotherapeutic agent is a small molecule compound that directly inhibits the topoisomerase activity of Top1 by binding to Top1 or a Top1-DNA complex. In specific embodiments, the Top1-targeting agent is a camptothecin (CPT) compound, or an analogue (such as topotecan and irinotecan), derivative, metabolite or mimetic thereof. Camptothecins are exceptional chemotherapeutic agents for use in the disclosed method as they easily penetrate mammalian cells where they readily target and bind Top1 with a high level of specificity and thus, inhibit the normal function of the Top1-DNA complex by converting Top1 from a topoisomerase to a strand-cleaving enzyme. Moreover, camptothecins can be provided in high dosages due to their high specificity to Top1.

The term "camptothecins" or "a camptothecin compound" refers to a family of quinoline alkaloid compounds, characterized by Formula I

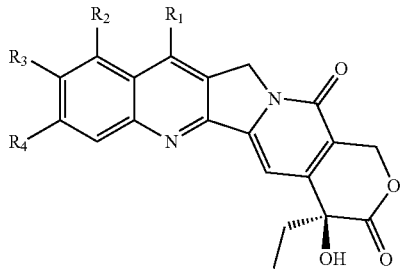

and analogs, derivatives, metabolites, pharmaceutical acceptable salts thereof. R1 can be selected, e.g., from alkyl groups, alkylsilyl groups, or nitrogen containing side chains, which may provide desirable cytotoxicity, stability and solubility, respectively; R2 and/or R3 can be selected from, e.g., an electron-withdrawing group; and $R_3$ and/or R4 can be selected from a hydroxyl group. Additionally, hexacyclic analogs resulting from modifications of Formula I by adding a methylenedioxy or ethylenedioxy group connecting $R_3$ and $R_4$ exhibit increased solubility and cytotoxicity. Specific camptothecin compounds suitable for use in this invention include the compound having the chemical name, (S)-4-ethyl-4-hydroxy-1H-pyrano[3',4':6,7]indolizino[1,2-b]quinoline-3,14-(4H, 12H)-dione (lactocamptothecin), topotecan hydrochloride (Hycamtin®), and irinotecan hydrochloride (Camptosar®), 9-NC Rubitecan (Orathecin), 9-AminoCPT, Exatecan mesylate, lurotecan, Gimatecan, prothecan, karenitecin, silatecan, diflomotecan (homocamptothecin) and its ketonic derivatives. Metabolites include, for example, SN-38 (active metabolite of irinotecan). Camptothecins further include pEGylated or nanoparticle bearing derivatives as well as derivatives attached to turmor-targeting antibodies, including but not limited to PEG-SN-38 and Labetuzumab-SN-38, respectively. For example, "PEG-campothecin" is a pEGylated derivative of the compound of Formula I. See review by Pommier, Y., Nature Reviews: Cancer. 6:789-802 (2006) for the camptothecin family of compounds, the contents of which are incorporated herein by reference.

Yet another aspect of the current method utilizes non-camptothecin Top1 inhibitors, including but not limited to, indolocarbazoles, 5,11-diketoindenoisoquinolines, and phenanthridines derivatives (topovale, nitidine).

Top1-directed therapeutic agents will also include pEGylated or nanoparticle bearing derivatives of Top1 inhibitors as well as Top1 inhibitors attached to tumor-targeting antibodies, including but not limited to PEG-SN-38 and Labetuzumab-SN-38, respectively.

In another embodiment of the current disclosure a Top1-directed chemotherapeutic agent may be identified by screening chemical libraries, novel compounds, and natural products with purified Top1 protein to identify agents that bind or form complexes with Top1.

The ability of a chemotherapeutic agent to target and effect Top1 and act as a chemotherapeutic agent can be determined using pharmacological models well known in the art for example, Top1-mediated DNA cleavage assays, cytotoxic assays, xenograft assays and binding assays.

A non-limiting example of a Top1-mediated DNA cleavage assay showing the efficacy of a compound of interest in nicking DNA includes, expressing Top1 in E. Coli and isolating said protein as a recombinant fusion protein using a T7 expression system. Next, Top1 protein can be purified using standard matters including but not limited to those described in Maniatis, T., et al., J. Molecular Cloning, a Laboratory Manual, Cold Spring Harbor Laboratory, Cold Spring Harbor, N.Y., 149-185. Plasmid DNA can also be purified by the alkali lysis method followed by phenol deproteination and CsCl/ethidium isopycnic centrifugation. The end-labeling of the plasmid can then be facilitated by digestion with a restriction enzyme followed by end-filling with Klenow enzyme. Cleavage assays can be performed according to known methods (see, e.g., B. Gatto et al. Cancer Res., (1996) 56:2795-2800). The compound of interest and the DNA in presence of topoisomerase I are then incubated for 30 minutes at 37° C. After development of the gels, typically 24-hour exposure can be used to obtain autoradiograms outlining the extent of DNA fragmentation.

The cytotoxic effects of a compound for use with the current method can also be determined using pharmacological models that are well known in the art, for example, cytotoxicity can be determined using the MTT-microtiter plate tetrazolinium cytotoxicity assay (MTA). The human cancer cell lines including but not limited to, MCF-10, MCF-7 and camptothecin-resistant variant cell lines, such as BT474 (ATCC), can be used to perform the cytotoxicity assay, that entails using 96-well microtiter plates; growing sells in suspension at 37° C. in 5% $CO_2$ and maintained by regular passage in RPMI medium supplemented with 10% heat inactivated fetal bovine serum, L-glutamine (2 mM), penicillin (100 U/mL), and Streptomycin (0.1 mg/mL). For determination of $IC_{50}$, cells can be exposed continuously for four days to varying concentrations of drug, and MTT assays can be performed at the end of the fourth day. Each assay should be performed with a control that did not contain any compound of interest The response of cells to a potential Top1-targeting therapeutic agent can be examined thus, identifying additional agents for use in the current method by seeding known cells into 96-well microplates. For example, when the cells completely attach to the plates, cells are treated with varying concentrations of a candidate agent. After 72 hours, 50 ml of XTT working solution is added to the each well, and then the microplate is incubated for 2 hours. The optical density can then be measured with a microplate reader. The survival of cells at each concentration of the candidate drug will be revealed as the percentage ratio of the optical density of cells treated with the target drug to the optical density of the untreated cells.

In an aspect of the current disclosure, a cancer in the methods as disclosed herein is any cancer which can be treated, or is desirable to be treated with a Top1 chemotherapeutic agent.

In specific embodiments, cancer is an adrenocarcinomas such as prostate cancer, ovarian cancer, breast cancer, colorectal cancer, or pancreatic cancer.

In another embodiment, the cancer is selected from a list consisting of, colorectal cancer, breast cancer, lung cancer, adenosquamous lung carcinoma, B-Cell acute lymphoblastic leukemia, bladder urothelial carcinoma, brain astrocytoma, breat adenocarcinoma, breast carcinoma, colon adenocarcinoma, colon carcinoma, ductal breast carcinoma, endometrial adenocarcinoma, endometrial endometrioid adenocarcinoma, esophageal squamous cell carcinoma, hepatocellular carcinoma, invasive ductal breast carcinoma, ovarian adenocarcinoma, rhabdomyosarcoma, squamous cell lung carcinoma, acute myeloid leukemia (AML), blast phase chronic myleogenous leukemia, brain glioblastoma, burkitts lymphoma, cutaneous melanoma, diffuse large B-cell lymphoma, gastric andenocarcinoma, gastric cancer, lung adenocarcinoma, melanoma, multiple myeloma, neuroblastoma, pancreatic adenocarcinoma, pancreatic ductal carcinoma, small cell lung carcinoma, T-cell acute lymphoblastic leukemia, and tongue squamous cell carcinoma.

According to the present methods, CUL4B expression is detected in a biological sample obtained from a subject, wherein an elevated level of CUL4B expression in the sample identifies the subject as resistant to Top1-directed chemotherapy.

A biological sample is obtained from the subject in question. The biological sample that can be used in accordance with the present disclosure may be collected by a variety of means that will depend on the type of cancer expressed by the subject. Non-limiting examples include surgical excision, endoscopic biopsy, excisional biopsy, incisional biopsy, fine needle biopsy, punch biopsy, shave biopsy and skin biopsy. Additionally, resection, bronchoscopy, fine needle aspiration, bronchial brushings, or from sputum, pleural fluid or blood. The expression of CUL4B can also be detected from cancer or tumor tissue or from other body fluid samples such as whole blood (or the plasma or serum fractions thereof) or lymphatic tissue. In some embodiments, the sample obtained from a subject is used directly without any preliminary treatments or processing, such as fractionation or extraction of DNA or RNA.

In other embodiments, the sample is processed such that DNA, RNA or proteins can be extracted or enriched from the sample before detecting CUL4B expression levels. Methods of extracting DNA from biological sample are well known in the art, and may be performed using, for example, phenol/chloroform, ethanol, or commercially available DNA extraction reagents. In certain aspects, a tumor or tumor biopsy is obtained from a subject and fluid from the tumor is removed, e.g., by centrifugation, and the tumor fluid is used as the sample for measuring CUL4B protein, mRNA or DNA.

In practicing the methods described herein, the level of CUL4B expression can be determined by any suitable method, e.g., DNA based methods or protein-based methods. Various methods of determining the level of expression of a gene of interest are known in the art.

The analysis of CUL4B expression can occur before or after a cancer diagnosis has been made and prior to, during or after the initiation of treatment with a Top1-directed chemotherapeutic agent. In another aspect, the analysis of CUL4B expression occurs after a cancer diagnosis has been made. In yet another aspect of the current disclosure, the analysis of CUL4B expression occurs with or after the initiation of treatment with a Top1-directed chemotherapeutic agent. In yet another aspect the analysis of CUL4B expression occurs after said cancer has been determined to be resistant to treatment with a Top1-directed chemotherapeutic agent.

CUL4B or cullin 4B (NG_009388) is member of the cullin gene family located on the X-chromosome (Xq23) spanning nucleotides 119658444-119709684 comprising 51240 base pairs. The CUL4B gene encodes for a protein which forms a complex with adaptor proteins including aryl hydrocarbon receptor that functions as an E3 ubiquitin ligase and catalyzes the polyubiquitination of specific protein substrates in the cell. The CUL4B protein interacts with a ring finger protein, and is required for the proteolysis of several regulators of DNA replication including chromatin licensing and DNA replication factor 1 and cyclin E. Multiple transcript variants encoding different CUL4B protein isoforms have been found.

In some embodiments, the level of CUL4B expression is determined based on detecting the level of CUL4B protein. CUL4B protein can be detected generally by contacting a biological sample with a reagent that forms a complex with the CUL4B protein and detecting the complex indicating the presence of the CUL4B protein. For example, the reagent may be a small molecule, peptide, nucleic acid or antibody that interacts with CUL4B protein. In many embodiments, the reagent is designed or prepared to permit detection of all CUL4B protein isoforms or variants present in the sample (e.g., the reagent being an antibody directed to epitopes common to all isoforms and variants). In other embodiments, the reagent is designed or prepared to permit detection of a particular CUL4B protein isoform.

In a specific embodiment of the current methods, the reagent is an antibody, a polyclonal or monoclonal antibody, which is raised against the N-terminal portion of CUL4B protein, e.g., amino acid residues 9-152 of SEQ ID NO: 3. A polyclonal antibody raised against this region of SEQ ID NO: 3 is believed to bind to SEQ ID NO: 8 as well. An example of such a polyclonal antibody is available from Novus Biochemicals, cat# NBP1-86099, which is highly specific for CUL4B and does not cross-react with CUL4A. In yet another embodiment of the current disclosure, the reagent is an antibody, either polyclonal or monoclonal antibody, which binds to a region common to all CUL4B protein forms, e.g., a monoclonal antibody available from ProteinTech Group, Inc., cat#60151-Ig.

Any of the antibodies for detecting CUL4B expression can be used alone or in combination in practicing the methods of the invention.

Non-limiting examples of CUL4B protein detection includes employment of an ELISA assay, Western blotting, immunohistochemistry or immunoprecipitation. Methods for these techniques are well known to those skilled in the art.

Western blotting can be performed as follows. A biological sample containing cells (e.g., tumor cells) is washed in phosphate buffered saline (PBS) and incubating on ice for 20 minutes in hyptonic buffer (10 mM Tris-HCl, pH8.0, 1 mM KCl, 1.5 mM $MgCl_2$, 1 mM DTT, freshly added protease inhibitor mixtures). Cells in the sample are then lysed and centrifuged at 6000 rpm at 4° C. for 10 minutes. The pellet is suspended in 0.4 ml 0.4N $H_2SO_4$ at 4° C. for overnight, and centrifuged at 13000 rpm for 10 minutes. Histones are precipitated from the supernatant by add 0.25 volume of 100% (w/v) ice cold trichloroacetic acid. The pellets are then washed by 100% cold ethanol (−20° C.) and centrifuged again at 13000 rpm for 5 minutes. The pellets are then dissolved in 560 ml RIPA buffer (150 mM NaCl, 50 mM HEPES, pH7.4, 0.5% Sodium Deoxycholate, 0.1% SDS, freshly added protease inhibitor mixtures) and 40 ml 10% SDS. Protein samples may then be used immediately or stored at −80° C. The proteins in the sample are then separated using SDS-PAGE and then transferred to a membrane for detection wherein, the membrane is incubated with a generic protein (such as milk proteins) to bind to any remaining sticky places on the membrane. A primary antibody recognizing CUL4B is then added to the solution; and finally a secondary antibody-enzyme conjugate, which recognizes the primary antibody bound to CUL4B is added to find locations where the primary antibody bound.

Enzyme-linked Immunosorbent Assays (ELISA) utilize the specificity of antibodies with the sensitivity of simple enzyme assays, by using antibodies or antigens coupled to an easily-assayed enzyme. An ELISA is typically a five-step procedure comprising, coating the microtiter plate wells with antigen; blocking all unbound sites to prevent false positive results; adding an antibody to the wells to detect the presence of CUL4B, for example Anti-CUL4B antibody (1216-1-AP Proteintech Group); incubating with anti-mouse, rabbit or goat IgG antibody conjugated to an enzyme such as horseradish peroxidase; and finally the reaction of a substrate with the enzyme to produce a colored product, thus indicating a positive reaction and the presence of CUL4B. The results of these actions may then be analyzed and quantified to determine relevant expressions levels by standard statistical techniques, including student's T-test.

Immunohistochemistry utilizes at least one anti-CUL4B antibody to detect the presence of CUL4B protein in sections obtained from tumors, including paraffin-embedded and frozen tumor sections. Typically, the tumor sections are initially treated in such a way as to retrieve the antigenic structure of proteins that were fixed in the initial process of collecting and preserving the tumor material. Slides are then blocked to prevent non-specific binding by the anti-CUL4B detection antibody using a blocking reagent such as bovine serum albumin (BSA) or non-fat dried milk. The presence of CUL4B protein is then detected by binding of the anti-CUL4B antibody to the CUL4B protein. The detection antibody is linked to an enzyme, either directly or indirectly, e.g., through a secondary antibody that specifically recognizes the detection antibody. Typically, the tumor sections are washed between steps. The slide is developed using an appropriate enzyme substrate to produce a visible signal, and the samples are then counterstained with hematoxylin.

In one aspect of the current disclosure, H-Score quantification analysis is used, whereby the intensity of the signal as well as the % tumors present in a biopsy sample are compared to quantify protein expression following immunohistochemistry.

The level of expression of CUL4B in a biological sample of the subject can also be determined, for instance, by flow cytometry, and the level of expression (e.g., staining intensity) can be correlated with responsiveness to treatment with a Top1-directed chemotherapeutic agent.

In another aspect, CUL4B expression can be analyzed by detecting CUL4B nucleic acids, either DNA or RNA. This can be achieved by contacting a sample with a nucleic acid reagent (e.g., a probe or a primer pair) that binds to a CUL4B nucleic acid molecule. In many embodiments, the nucleic acid reagent is designed or prepared to permit detection of all CUL4B transcript isoforms or variants present in the sample (e.g., the reagent being a probe or primer pair designed to bind to a nucleic acid portion common to all CUL4B isoforms and variants, such as a primer which binds to the 3' portion common to all mRNA transcripts for use in a RT-PCR). In other embodiments, the reagent is designed or prepared to permit detection of a particular CUL4B transcript isoform. Non-limiting examples of nucleotide detection techniques for use with the current method include, Southern blotting, northern blotting, quantitative real-time PCR, reverse transcriptase PCR ("RT-PCR"), single nucleotide polymorphism (SNP) DNA microarray, Next-Gen sequencing, and fluorescence in-situ hybridization (FISH).

Southern blotting generally facilitates the determination of the molecular weight of DNA sequence and the measurement of relative amounts of a DNA sequence of interest in different samples. For example, Southern blotting comprises digesting DNA from a biological sample with a restriction enzyme or restriction enzymes and separating the DNA via gel electrophoresis on an agarose gel. The DNA is then denatured to form single-stranded DNA using NaOH and then transferred to a membrane retaining the same pattern of fragmentation exhibited on the agarose gel. The blot is then incubated with many copies of a single-stranded DNA probe that is complementary to the DNA sequence of interest and either radioactive or enzyme bound (e.g. alkaline phosphatase or horseradish peroxidase) to enable identification. Finally, the location of the probe is revealed by incubating it with a colorless substrate that the attached enzyme converts to a colored product that can be seen or gives off light which will expose X-ray film. If the probe was labeled with radioactivity, it can expose X-ray film directly.

Quantitative real-time PCR utilizes a detection system, such as ABI PRISM® 7700 Sequence Detection System, available from PE-Applied Biosystems, Foster City, Calif. and used according to manufacturer's instructions. PCR reagents can be obtained from PE-Applied Biosystems, Foster City, Calif. Gene target quantities obtained by real time RT-PCR may be normalized using either the expression level of a gene with constant expression (Control expression) including but not limited to, GAPDH or α-tubulin, or by quantifying total RNA using RiboGreen™ (Molecular Probes, Inc. Eugene, Oreg.). Control expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones et al. (1998). Controls are analyzed in parallel to verify the absence of DNA in the RNA preparation (-RT control) as well as the absence of primer dimers in control samples lacking template RNA. In addition, RT-PCR products may be analyzed by gel electrophoresis.

A gene copy number analysis can be utilized within the current method to determine CUL4B expression in a subject. Generally, gene copy number can be quantitated using real-time quantitative PCR. The method involves relative quantification of the gene of interest, CUL4B, versus a reference gene known to be single copy. Relative quantity is determined by the ΔΔCt method (see, e.g., Livak K. J. and Schmittgen T. D. *Methods* (2001) 25: 402-408), where the calibrator is a control sample used as the basis for comparative results. Gene copy number is 2× relative quantity. A non-limiting example of a gene copy number analysis is as follows, primers and probes are designed based on genomic DNA template sequence to recognize the gene of interest, CUL4B. For each biological sample a 20 µl assay comprising 10 ng of gDNA, 900 nM each of forward and reverse primers for the reference gene (RNaseP) and for the target gene, CUL4B, 250 nM each of the VIC® dye and FAM™ dye-(target) labeled gene-specific probe in 1× TaqMan® Universal Master Mix. Thermal-cycling conditions (7900HT) were: 2 mins at 50° C., 10 mins at 95° C., followed by 40 cycles of 15 secs at 92° C. and 60 seconds at 60° C. Real-time data was collected by the SDS 2.1 software. Each replicate was normalized to RNaseP to obtain a ΔCt (FAM dye Ct-VIC dye Ct), and then an average ΔCt for each sample (from the 4 replicates) was calculated. All samples were then normalized to a control sample to determine ΔΔCt. Relative quantity (RQ) is 2-ΔΔCt, and copy number is 2×RQ. Quantitative real-time PCR to determine gene copy number can be used to confirm a gene copy number polymorphism and as such gene copy number.

Single nucleotide polymorphism microarrays can be used to analyze genome wide copy number variation in a subject according to many techniques known to one skilled in the art (See, e.g., Huang J., et al., *Hum. Genomics* (2004) 1:287-299). A non-limiting example includes, isolating genomic DNA from a subject using standard techniques, including but not limited to, blood extraction, tissue scraping, and biopsy. Microarray experiments can then be performed analyzing samples obtained from cancer subjects and control samples according to manufacturers (Affymetrix, Inc., Santa Clara, Calif.) protocols for Affymetrix 100k SNP array contains 25-mer oligonucleotides representing a total of 116,204 SNPs, distributed over two microarrays or Affymetrix 250k SNP array providing two microarrays each containing approximately 250,000 SNPs together forming a 500k SNP analysis assay, GoldenGate genotyping microarray (Illumina Inc.), Infinium genotyping microarray (Illumina Inc.). Copy-number estimations can then be determined using known software programs, including but not limited to, CNAG (Copy Number Analyzer for Affymetrix GeneChip Mapping 100k arrays) (See, Nannya Y., et al., *Cancer Res*. (2005) 65:6071-6079), a statistical power analysis comprising, a determination of the distribution of the noise, establishment of estimates for significant changes and the variance of noise within each experiment, calculation of the number of data points required for detection of copy-number variations, and determination of the resolution of a microarray platform (See, Hehir-Kwa, J Y, et al., *DNA Research* (2007), 14(1): 1-11).

As demonstrated herein, significant alterations in CUL4B expression levels have been observed in cancer samples relative to control which have been correlated to the resistance or responsiveness of the cancerous cells to treatment with a Top1-directed chemotherapeutic agent.

In one embodiment, CUL4B expression measured from the subject in question, generally a subject having cancer, is compared to a control value in order to determine whether or not the subject will likely be responsive to treatment with a Top1-directed chemotherapeutic agent. To assess the relative level of CUL4B expression, the level of CUL4B expression in a cancer tissue sample obtained from the subject can be subjected to one or more of various comparisons. In general, it can be compared to: (a) CUL4B expression level(s) in normal tissue from the organ in which the cancer originated (e.g., colon, breast or lung tissue); (b) CUL4B expression levels in a collection of cancer tissue samples which have been characterized as responsive to Top1-targeting chemotherapeutic agents; (c) CUL4B expression level(s) in a collection of normal, non-cancerous tissue samples; or (d) CUL4B expression level(s) in an arbitrary standard. A control value can be a pre-determined value or can be determined from a control sample side by side with the sample obtained from the subject in question.

In a specific embodiment, the control value is established from a control sample obtained from normal or benign tissue, for example, benign tissue of the organ from which the cancer originated.

According to the current disclosure, the amount of CUL4B expression in a test sample is analyzed and compared to level of CUL4B expression from a control sample (e.g., a sample from benign tissue or surgical margins), and the difference in CUL4B expression levels between the test sample and the control can be determined. An elevated level of CUL4B expression is evidenced by a significant increase in CUL4B expression of a test sample relative to a control, which indicates that the test subject is not likely to be responsive to treatment with a Top1-directed chemotherapeutic agent.

Non-limiting examples of a significant increase in CUL4B mRNA or protein expression levels, include but are not limited to, 2%, 3%, 4%, 5%, 6%, 7%, 8%, 9%, 10%, 15%, 20%, 30%, 40%, 50%, 60%, 70%, 80%, 90%, 100%, 200%, 300%, 400% or more, over that of a control. Non-limiting examples of a significant increase in CUL4B gene copy number as a measure of CUL4B expression, include but are not limited to, 1-2, 1-10, 3-5 copies, 4-6 copies, or more, over that of a control.

Classification of patients based on CUL4B expression levels not only predicts the patient's responsiveness to Top1-directed chemotherapy, but also permits personalized design of treatment options. For example, for subjects identified as having CUL4B expression levels that are reduced or equal to that of a control level, a Top1-directed chemotherapy is expected to be effective and can be administered. For subjects identified as having CUL4B expression levels that are elevated relative to control, the subjects will likely not be responsive to Top1-directed chemotherapy. However, these subjects can be treated with a CUL4B inhibitor as described hereinbelow, which sensitizes the subjects to Top1-directed chemotherapy.

Therapeutic Methods

The current disclosure shows that CUL4B protein directly interacts with Top1 in the presence of a Top1-targeting inhibitor as the two proteins were co-immunoprecipitated in vitro and CUL4B was again detected in the anti-Top1 antibody immunoprecipitate. Additionally, the current disclosure shows that CUL4B silencing by shRNA, sensitized cells that expressed elevated levels of CUL4B to treatment with a Top1-directed chemotherapeutic agent by increasing double stranded DNA breaks, limiting the Mre11-Chk1 DNA damage checkpoint response to the double stranded DNA breaks and increasing PARP mediated apoptosis.

Thus, the disclosure further provides a method of treating cancer in a subject who has been identified as expressing an elevated level of CUL4B, by administering to the subject an effective amount of an agent that inhibits expression or activity of CUL4B (a "CUL4B inhibitor"), wherein inhibition of expression of CUL4B sensitizes the cancer to the Top1-directed chemotherapeutic compound.

In one embodiment of the current disclosure, the CUL4B inhibitor is a nucleic acid, a small molecule, an antibody or a peptide, any of which directly or indirectly inhibits the expression or activity of CUL4B.

Within the scope of the current disclosure, an effective amount of a CUL4B inhibitor that reduces the level of expression or activity of CUL4B so as to sufficiently sensitize cancer to treatment with a Top1-directed chemotherapeutic agent is an amount that reduces the elevated level of CUL4B expression present in a subject to a level equal to or reduced when compared to a control. A reduction of CUL4B expression levels or activity can be achieved in many different ways. For example, it is possible to interfere with CUL4B expression by: 1) interacting with DNA sequences that will effect transcription of CUL4B RNAs, 2) interacting with CUL4B mRNA transcripts in a manner that reduces translation of functional CUL4B proteins, 3) by directly or indirectly impairing the activity of CUL4B (e.g. targeting CUL4B with an antibody that binds directly to the CUL4B protein or a portion thereof, or providing an agent that interacts with an effector of CUL4B and interferes with the interaction of CUL4B with Top1).

In some embodiments, the CUL4B inhibitor is an isolated nucleic acid that modulates the level of CUL4B expression in the subject being treated. In a specific embodiment, the isolated nucleic acid is a short hairpin RNA (shRNA), siRNA, or nucleic acid complementary to CUL4B mRNA. In certain embodiments, the shRNA or siRNA that inhibit CUL4B can be designed by one of ordinary skill in the art, using known methods to include a CUL4B targeting sequence, e.g., a sequence coding for the start or stop of transcription. Examples of suitable targeting sequences include TTTACCCTCTTTAAATTCTGC [SEQ ID NO. 6] or TAAACCTTTCTGAAGAATTGC [SEQ ID NO. 7]. Non-limiting examples of isolated nucleic acids suitable for use as CUL4B inhibitors include, [SEQ ID NO. 1] or [SEQ ID NO. 2] or an isolated nucleic acid that is substantially identical to [SEQ ID NO. 1] or [SEQ ID NO. 2].

In other embodiments, the CUL4B inhibitor is an antibody that binds CUL4B and interferes with the activity of CUL4B with Top1. The functional domains of the CUL4B protein have been well characterized, including a nuclear localization signal at the N-terminus, a DDB1 binding domain, a Cullin homology domain for binding Rbx1 adaptor, and a Neddylation domain at the C-terminus (see, e.g., Lee and Zhou, *Mol. Cell* 26, 775-80, 2006). An antibody can be raised against any of these functional domains, as well as regions outside of these functional domains, for purposes of interfering with the activity of CUL4B.

In specific embodiments, a CUL4B inhibitor is administered to a subject before, during (including simultaneously with), or after the treatment with a Top1-directed therapeutic agent.

In other embodiments, an additional therapeutic treatment is provided to the subject including administration of a chemotherapeutic agent independent of a CUL4B inhibitor and a Top1-directed inhibitor, and radiation, among others.

In the context of a combination therapy (i.e., involving a CUL4B inhibitor in combination with a Top1-directed chemotherapeutic compound, and optionally another independent chemotherapeutic agent), the CUL4B inhibitor may be administered before, during, or after commencing therapy with a Top1-directed chemotherapeutic compound, or an additional chemotherapeutic agent, as well as any combination thereof, i.e., before and during, before and after, during and after, or before, during and after commencing the additional chemotherapeutic treatment.

A suitable therapeutic agent of the current disclosure may be administered within a pharmaceutically-acceptable diluents, carrier, or excipient, in unit dosage form. As described herein, if desired, treatment with an isolated nucleic acid molecule of the current disclosure may be combined with therapies such as, for example, radiotherapy, surgery, among others.

The dosage of an agent that is administered to a subject in need thereof may vary, depending on the reason for use and the individual subject. The dosage may be adjusted based on the subject's weight, the age and health of the subject, and tolerance for the agent.

The amount of an agent of the current disclosure to be used depends on many factors. Dosages may include about 2 mg/kg of bodyweight/day, about 5 mg/kg of bodyweight/day, about 10 mg/kg of bodyweight/day, about 15 mg/kg of bodyweight/day, about 20 mg/kg of bodyweight/day, about 25 mg/kg of bodyweight/day, about 30 mg/kg of bodyweight/day, about 40 mg/kg of bodyweight/day, about 50 mg/kg of bodyweight/day, about 60 mg/kg of bodyweight/day, about 70 mg/kg of bodyweight/day, about 80 mg/kg of bodyweight/day, about 90 mg/kg of bodyweight/day, about 100 mg/kg of bodyweight/day, about 125 mg/kg of bodyweight/day, about 150 mg/kg of bodyweight/day, about 175 mg/kg of bodyweight/day, about 200 mg/kg of bodyweight/day, about 250 mg/kg of bodyweight/day, about 300 mg/kg of bodyweight/day, about 350 mg/kg of bodyweight/day, about 400 mg/kg of bodyweight/day, about 500 mg/kg of bodyweight/day, about 600 mg/kg of bodyweight/day, about 700 mg/kg of bodyweight/day, about 800 mg/kg of bodyweight/day, and about 900 mg/kg of bodyweight/day. Routine experimentation may be used to determine the appropriate value for each patient by monitoring the compound's effect on CUL4B levels or activity or Top1 levels or activity, or the disease pathology, which can be frequently and easily monitored. The agent can be administered once or multiple times per day. The frequency of administration may vary from a single dose per day to multiple doses per day. Routes of administration include oral, intravenous and intraperitoneal, but other forms of administration may be chosen as well.

The effective amount of an agent according to the present disclosure may be administered along any of the routes commonly known in the art. This includes, for example, (1) oral administration; (2) parenteral administration, for example, by subcutaneous, intramuscular or intravenous injection; (3) topical administration; or (4) intravaginal or intrarectal administration; (5) sublingual or buccal administration; (6) ocular administration; (7) transdermal administration; (8) nasal administration; and (9) administration directly to the organ or cells in need thereof.

The effective amount of an agent according to the present disclosure may be formulated together with one or more pharmaceutically acceptable excipients. The active ingredient and excipient(s) may be formulated into compositions and dosage forms according to methods known in the art. These compositions and dosage forms may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or stearic acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Excipients are added to the agent for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical agents that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subject's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid agent and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present disclosure, the agent and any other solid excipients are dissolved or suspended in a liquid carrier such as water, water-for-injection, vegetable oil, alcohol, polyethylene glycol, propylene glycol or glycerin. Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol. Liquid pharmaceutical compositions of the present disclosure may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Flavoring agents and flavor enhancers may make the dosage form more palatable to the patient. Common flavoring agents and flavor enhancers for pharmaceutical products that may be included in the composition of the present disclosure include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present disclosure, a liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present disclosure may be a capsule containing the composition, for example, a powdered or granulated solid composition of the disclosure, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting; however, they are not subjected to a final tableting step.

EXAMPLES

The following examples further illustrate the disclosure, but should not be construed to limit the scope of the disclosure in any way.

Example 1. CUL4B Expression is Elevated in Cancer Tissue

Tissue microarrays were generated for 138 cases of colorectal and 185 lung cancer patient samples including 72 samples derived from subjects diagnosed with small cell lung cancer, 113 cases derived from subjects diagnosed with squamous cell carcinomas. CUL4B expression levels were measured by immunohistochemistry using a polyclonal antibody specific for CUL4B and revealed that CUL4B expression was elevated in approximately 39% of colorectal and approximately, 40% of lung cancer patients tested (36% in small cell lung cancer (26/72), 41.6% (47/113) in squamous cell lung cancer). The data also revealed that an additional 45% of the 138 colorectal samples analyzed exhibited an elevated level of CUL4B expression when compared to control however the degree of increased expression did not result in an H-score of greater than 150.

Additionally, gene copy number was analyzed in 617 cancer samples representative of 36 different types of cancer (Table 1) using single nucleotide polymorphism (SNP) DNA microarray and fluorescence in-situ hybridization (FISH). The data revealed that 48% of the individual patient samples analyzed exhibited elevated CUL4B expression via increased gene copy number when compared to the normal copy number exhibited in non-cancerous controls.

For colon cancer, additional twenty colon cancer specimens were obtained, frozen and analyzed for CUL4B protein expression levels when compared to non-cancerous control tissue (surgical margins, benign samples) samples obtained from each subject (FIG. 6). Western blotting using a CUL4B antibody revealed that CUL4B expression was elevated in 45% (9 of 20 samples) of tumor samples when compared to non-cancerous benign surgical margin tissue extracted from the same subject.

In one aspect of the current disclosure it was determined that an elevated level of CUL4B ubiquitin ligase expression was found in breast cancer cell lines. Here, the expression levels of CUL4A or 4B were measured in a panel of breast cancer cells by Western Blotting. The expression levels of CUL4A and 4B varied to different extents in comparison to that of the immortalized MCF10A mammary epithelial cells. However, CUL4B expression was elevated in BT474, BT20 cells, and in SKBR3 cells (FIG. 1A). In contrast, CUL4A exhibited an elevated level of expression in T47D cells, but expression was not elevated in BT474 cells.

Figure 1B:
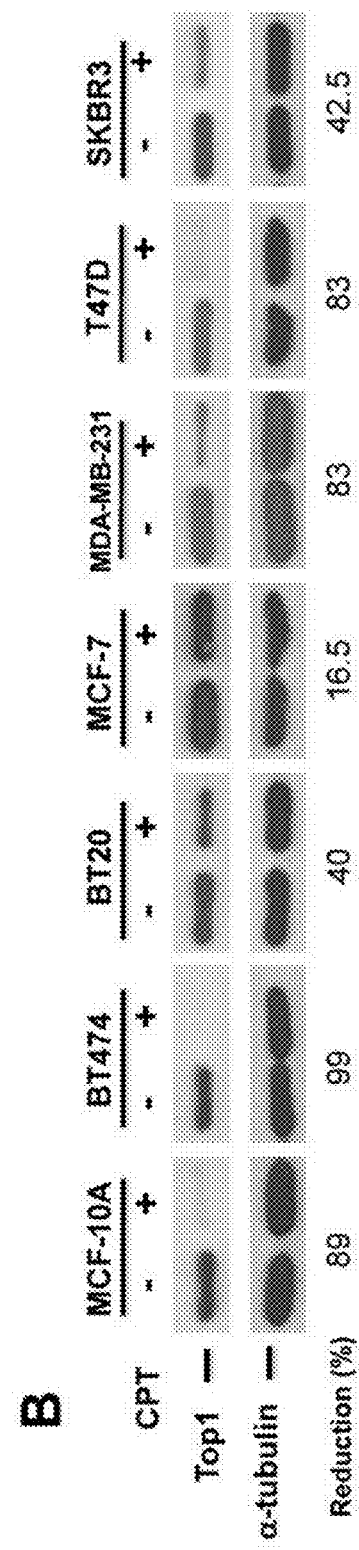

In response to camptothecin (CPT) treatment, DNA topoisomerase I (Top1) is degraded by the 26S proteasome. Here the sensitivity of Top1 destruction was analyzed in view of the expression levels of CUL4A and CUL4B. As shown in FIG. 1B, breast cancer cells exhibiting elevated levels of CUL4B expression eliminated or markedly destroyed Top1 following treatment with CPT.

Example 2. CUL4B Silencing Delays CPT-Induced TOP1 Degradation

Figure 2A:
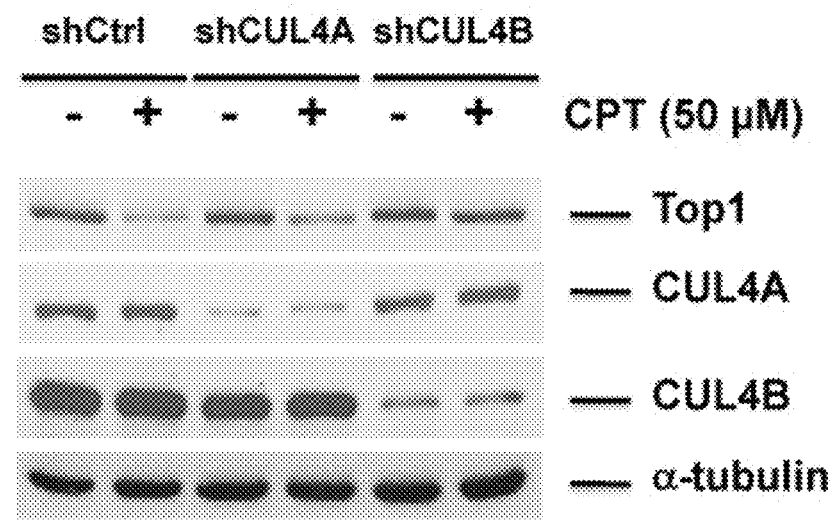
Figure 2B:
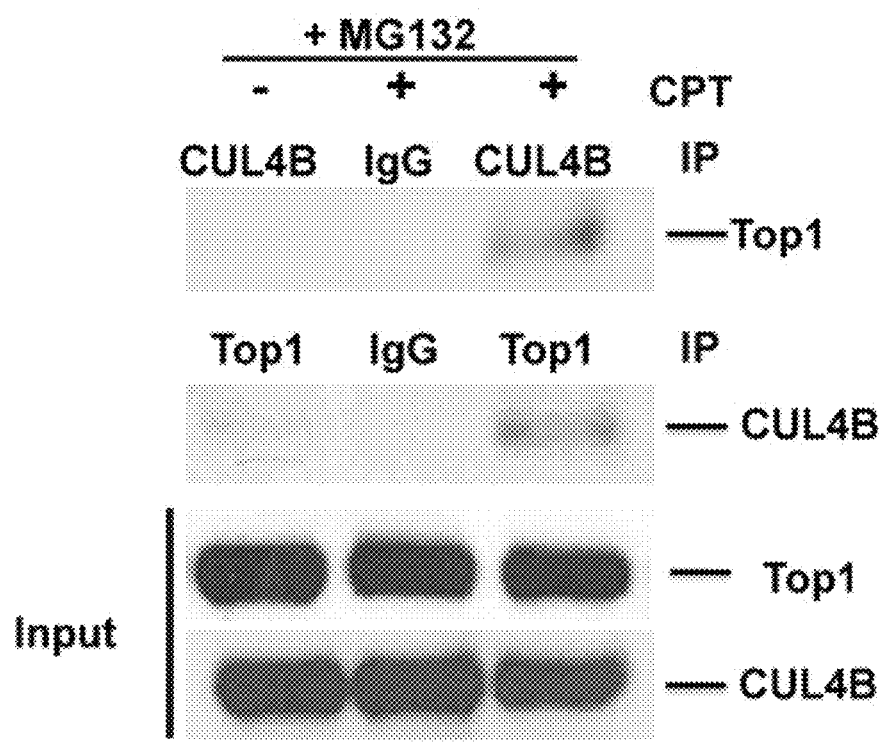

In one aspect of the current disclosure the relative contribution of CUL4A and CUL4B E3 ligases on CPT-induced Top degradation was analyzed. Here endogenous CUL4A and/or CUL4B was knocked down in BT474 and T47D cells by the application of shRNAs via lentiviral delivery and the effect of Top1 turnover was analyzed. As shown in FIGS. 2A and 2E, CPT-induced Top1 degradation was abolished in CUL4B-silenced (CUL4B$^{k/d}$) BT474 cells while CUL4A expression remained unaltered. Further, CUL4A had no effect on Top1 degradation when compared to the control (shCtrl) (FIG. 2A). Taken together, these data indicate that CUL4B and not CUL4A mediate CPT-induced Top1 degradation in breast cancer cell lines.

Example 3. CUL4B Directly Interacts with Top1 Following CPT Treatment

Next, it was determined that CUL4B directly binds to Top1 resulting in Top1 ubiquitination and degradation. In order to validate the physical interaction between CUL4B and Top1, mock- or CPT-treated BT474 cells were subjected to crosslinking with formaldehyde following treatment with CPT. Total protein extracts were isolated for co-immunoprecipitation with anti-CUL4B antibody followed by immunoblotting with an anti-Top1 antibody. As shown in FIG. 2B, Top1 was co-immunoprecipitated with CUL4B in the presence of CPT. Further evidence of the direct interaction is shown by the detection of CUL4B in the immunoprecipitation fractions analyzed by application of an anti-Top1 antibody. Notably, there was no detectable interaction between Top1 and CUL4B in the absence of CPT (FIG. 2B, Left lane). Therefore, the direct interaction between CUL4B and Top1 is dependent upon CPT treatment.

Example 4. CUL4B Silencing Increases CPT-Induced Cytotoxicity

Figure 2C:
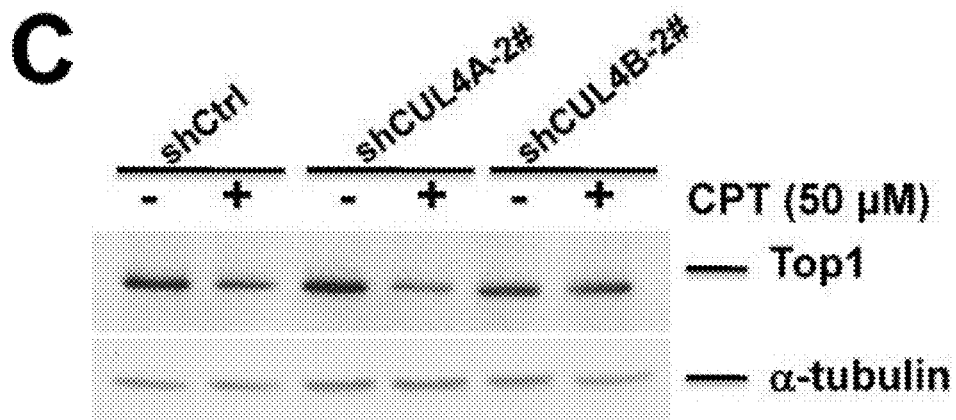
Figure 2D:
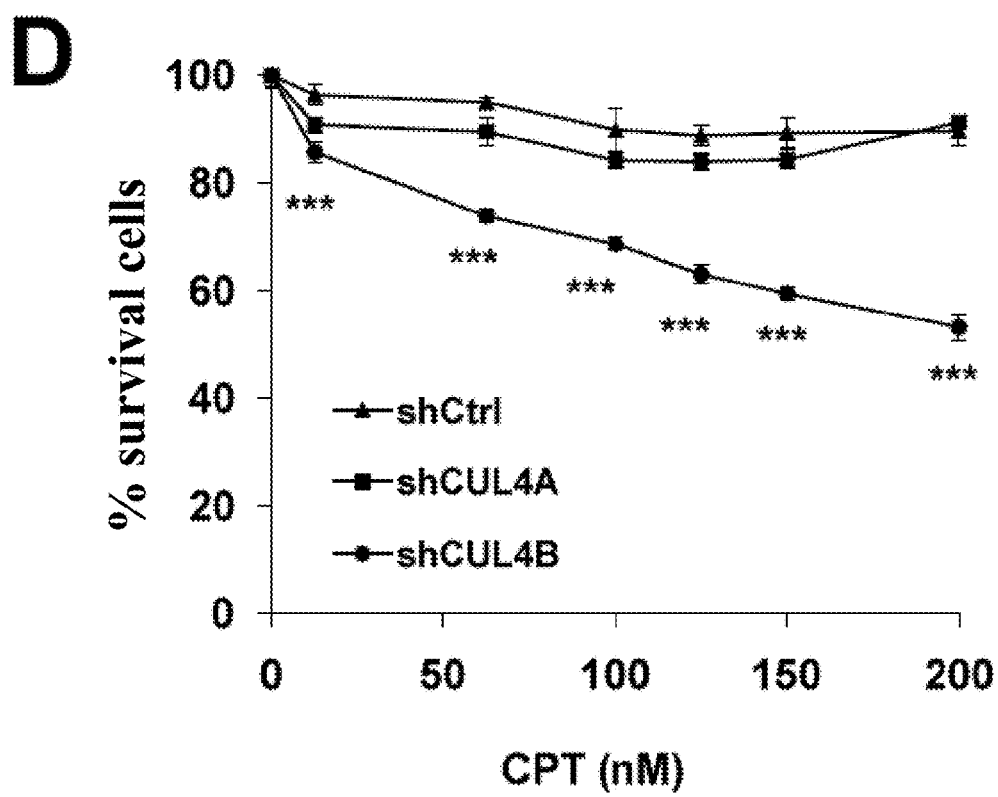
Figure 2E:
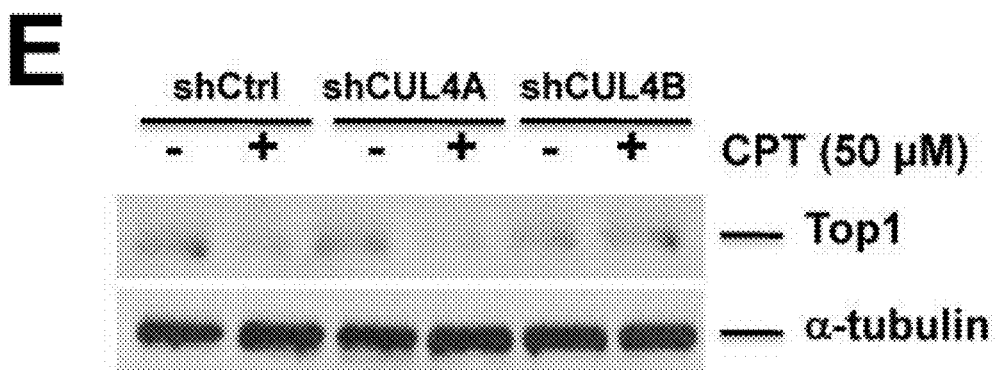
Figure 2F:
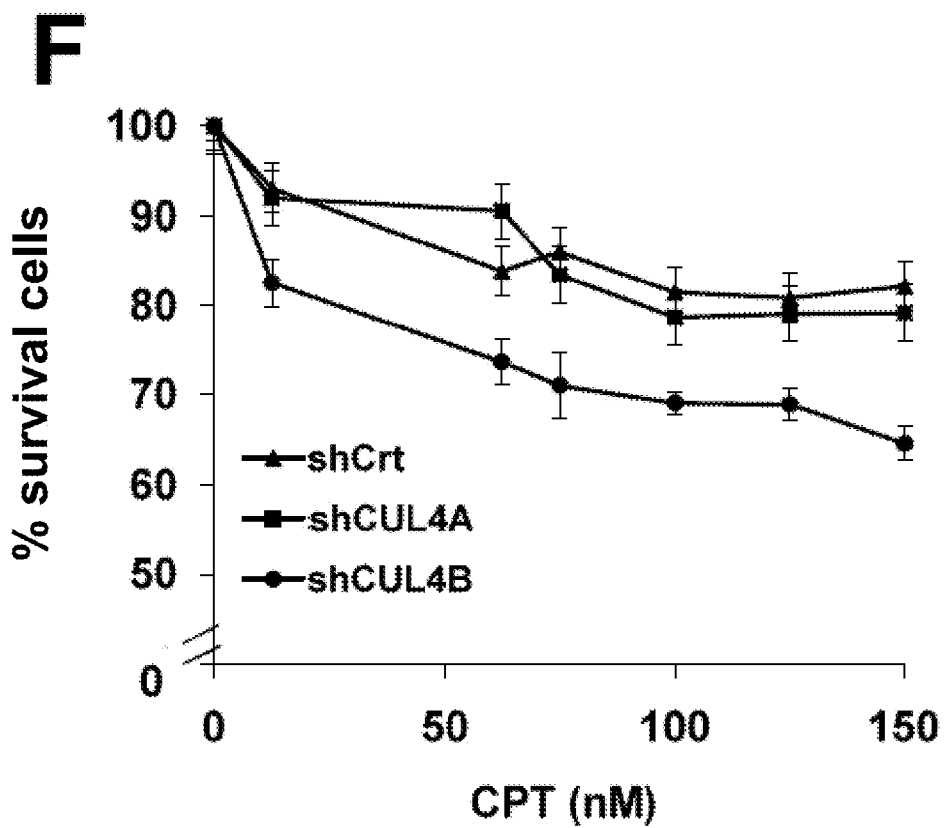

The data above show that CUL4B is involved in Top1 degradation in CPT-treated cells (FIGS. 2A, 2C and 2E). Thus, the inventors examined whether CUL4B inactivation enhances CPT cytotoxicity in CUL4B elevated breast cancer cells. The survival rate of BT474 and T47D cells exposed to CPT examined and revealed that knockdown of CUL4B, but not CUL4A, sensitized BT474 and T47D cells to cytotoxic killing by CPT (FIGS. 2D and 2F). Surprisingly, knockdown of CUL4A had no effect on the survival rate of CPT-treated cells contrary to what was reported previously. (See, Kerzendorfer et al., Human Molecular Genetics, (2010), 19:7).

Example 5. CUL4B Silencing Increases DNA Damage

Figure 3A:
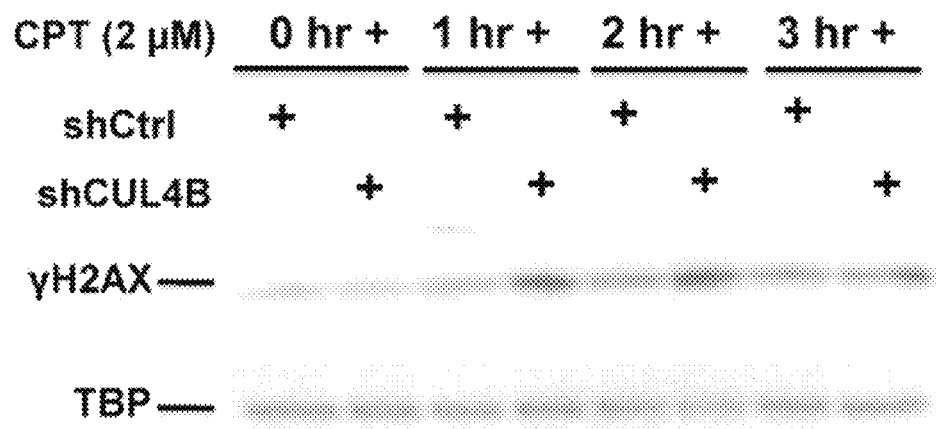
Figure 3B:
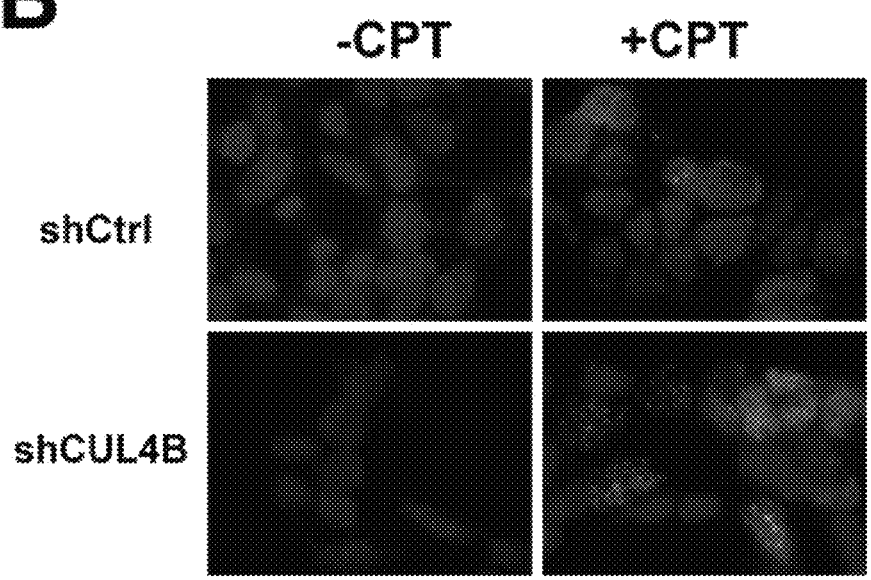
Figure 3C:
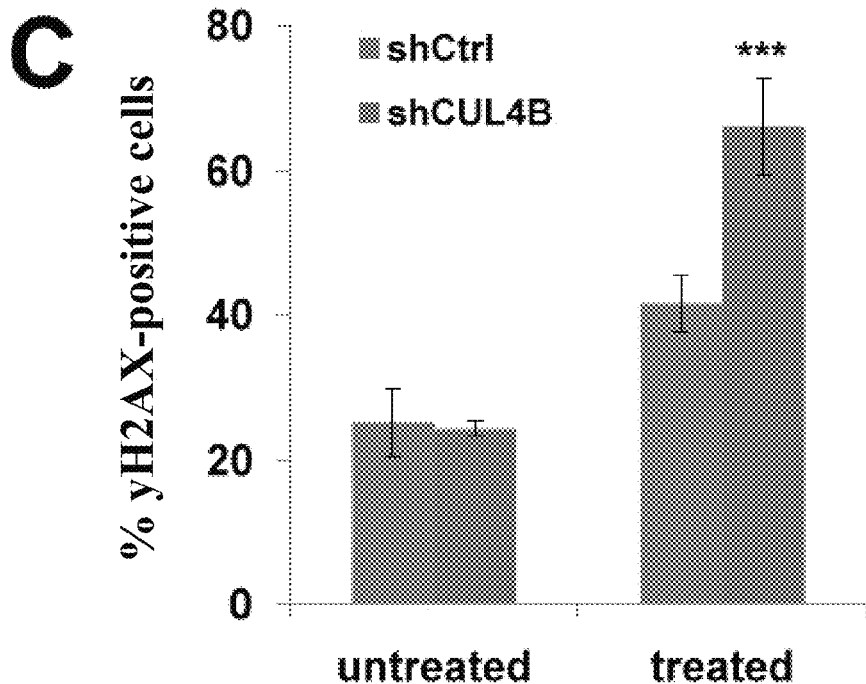
Figure 3D:
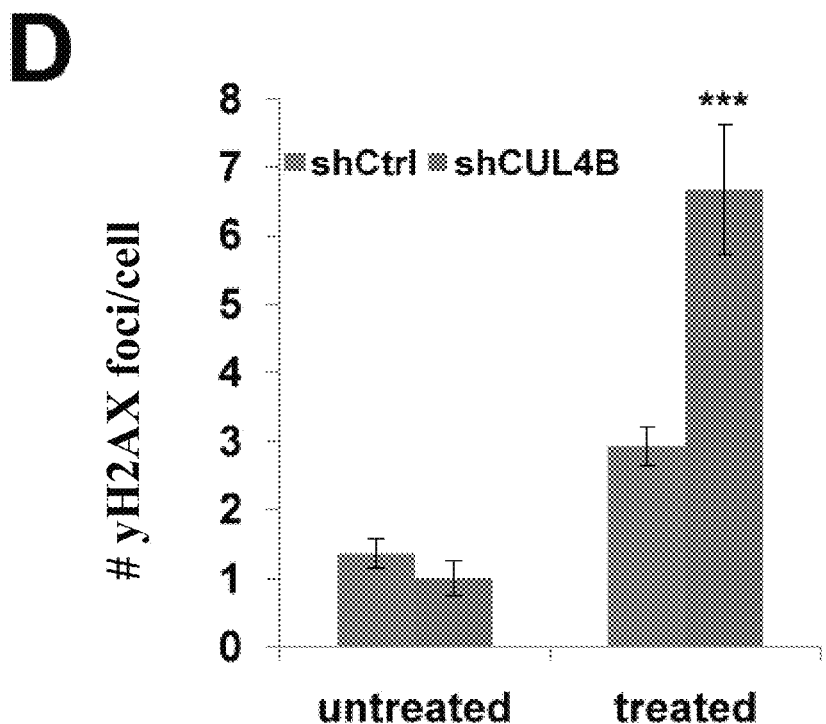
Figure 3E:
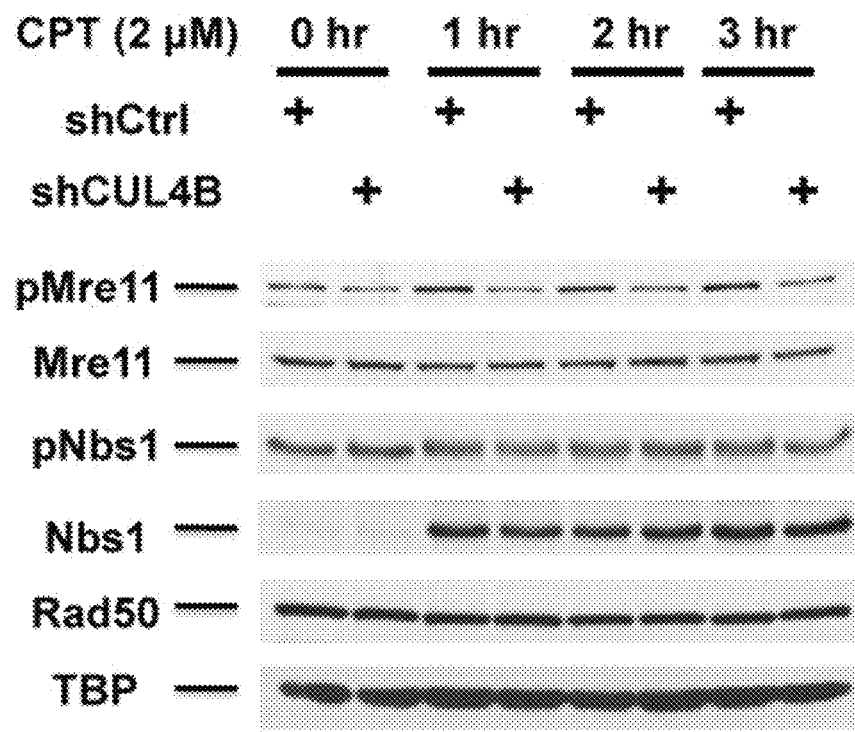
Figure 3F:
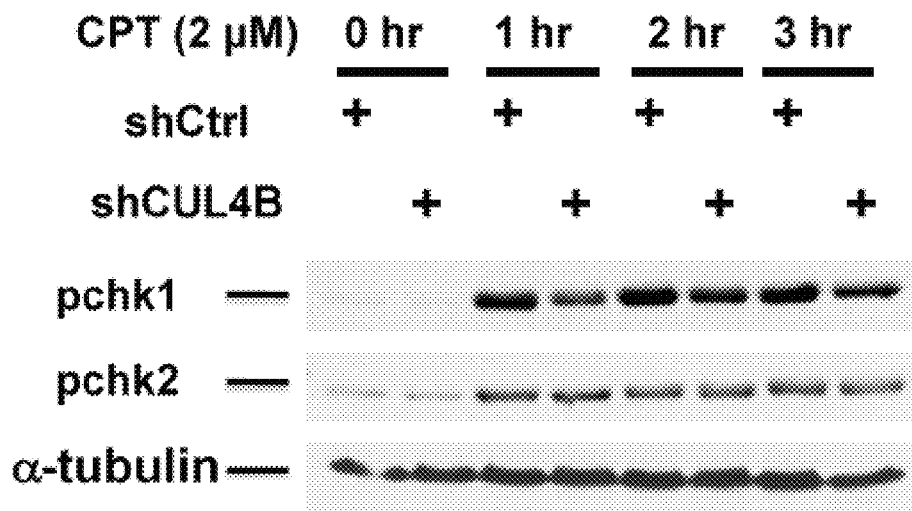

Next, it was shown that a reduction in CUL4B levels lead to increased CPT cytotoxicity. Double strand DNA breaks (DSBs) are indicated by increased accumulation of γH2AX foci on DNA. Here, both Western Blotting and immunofluorescent staining assays were utilized to detect γH2AX in cells immediately following CPT treatment and 1-3 hours after treatment, a time when DNA DSBs are repaired. As shown in FIG. 3A, CUL4B silencing via shRNA elevated the levels of γH2AX in CPT-treated BT474 cells, as detected by Western Blotting with an anti-γH2AX antibody. Additionally, immunofluorescent staining revealed significantly increased accumulation of γH2AX foci in 50% CPT-treated CUL4B$^{k/d}$-BT474 cells compared with 20% CPT-treated control cells (FIG. 3B-3D). Furthermore, inactivation of CUL4B attenuated the Mre11-Chk1 DNA damage checkpoint, as shown by the reduced phosphorylation of Mre11 and chk1 (FIG. 3E-F). These results reveal that CUL4B plays a role in enhancing DNA damage checkpoint response and repair, thereby protecting breast cancer cells from accumulating DSBs following CPT treatment.

Example 6. CUL4B Silencing Increases CPT-Induced Apoptosis

DNA double stranded breaks are one of the most cytotoxic lesions as persistence of γH2AX foci after the initial induction of DNA damage leads to apoptosis. To examine whether CUL4B knockdown affects the sensitivity of breast cancer cells to CPT-induced apoptosis, BT474 cells were treated with CPT and analyzed for induction of apoptosis, as exemplified by cleavage of caspase-3 and PARP. As shown in FIG. 4, silencing of CUL4B resulted in robust induction of apoptosis, as detected by Western blotting of cleaved caspase-3 and PARP post-CPT treatment when compared to that in control cells. Taken together, these data indicate that tumor cells with high levels of CUL4B expression are better protected from CPT-induced apoptosis and as such less likely to respond to therapeutic treatment with CPT.

Example 7. CUL4B Silencing Enhances the Antitumor Effects of Topotecan

Figure 5A:
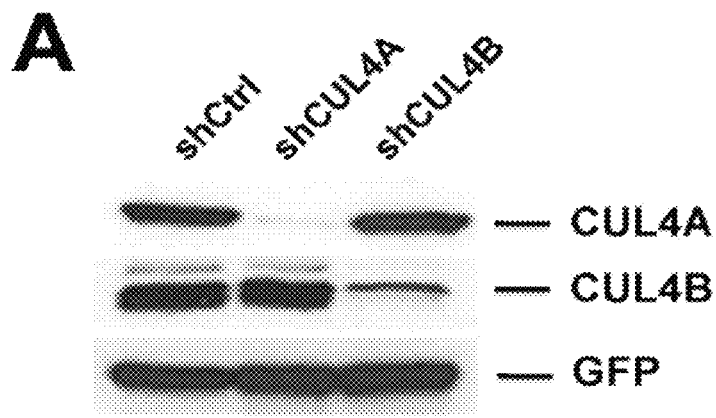
Figure 5B:
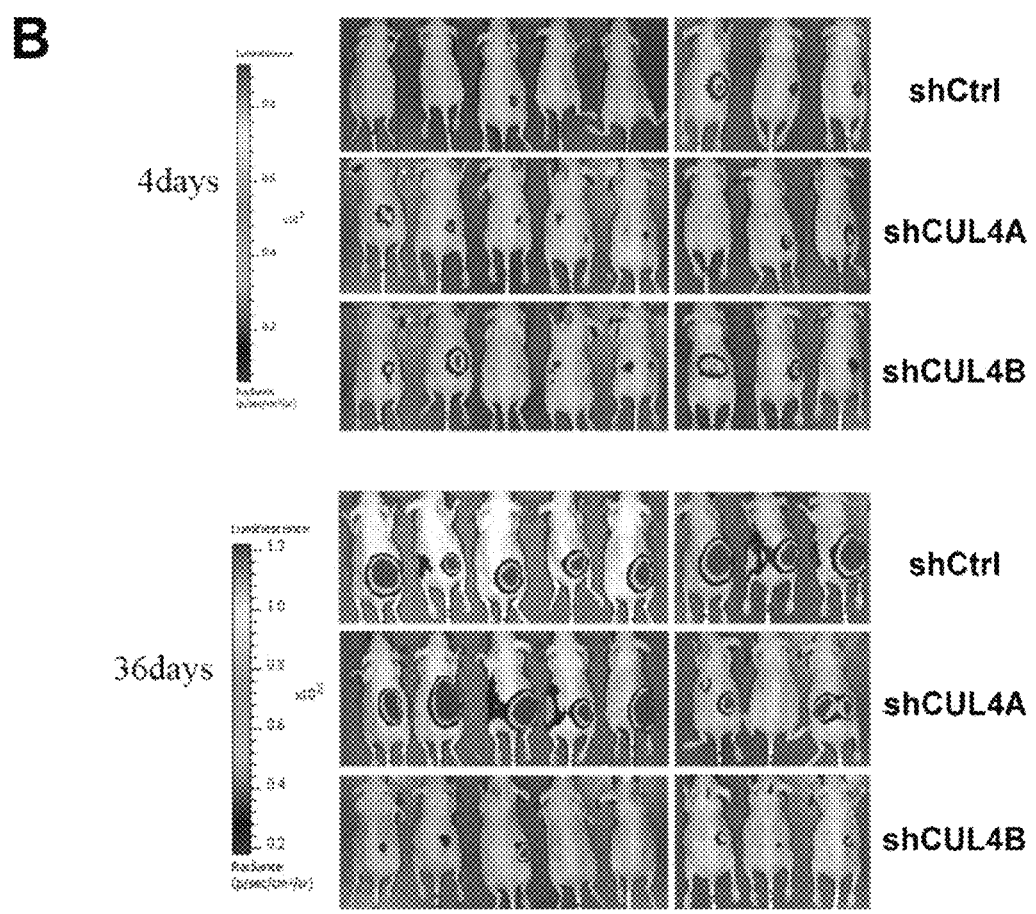
Figure 5C:
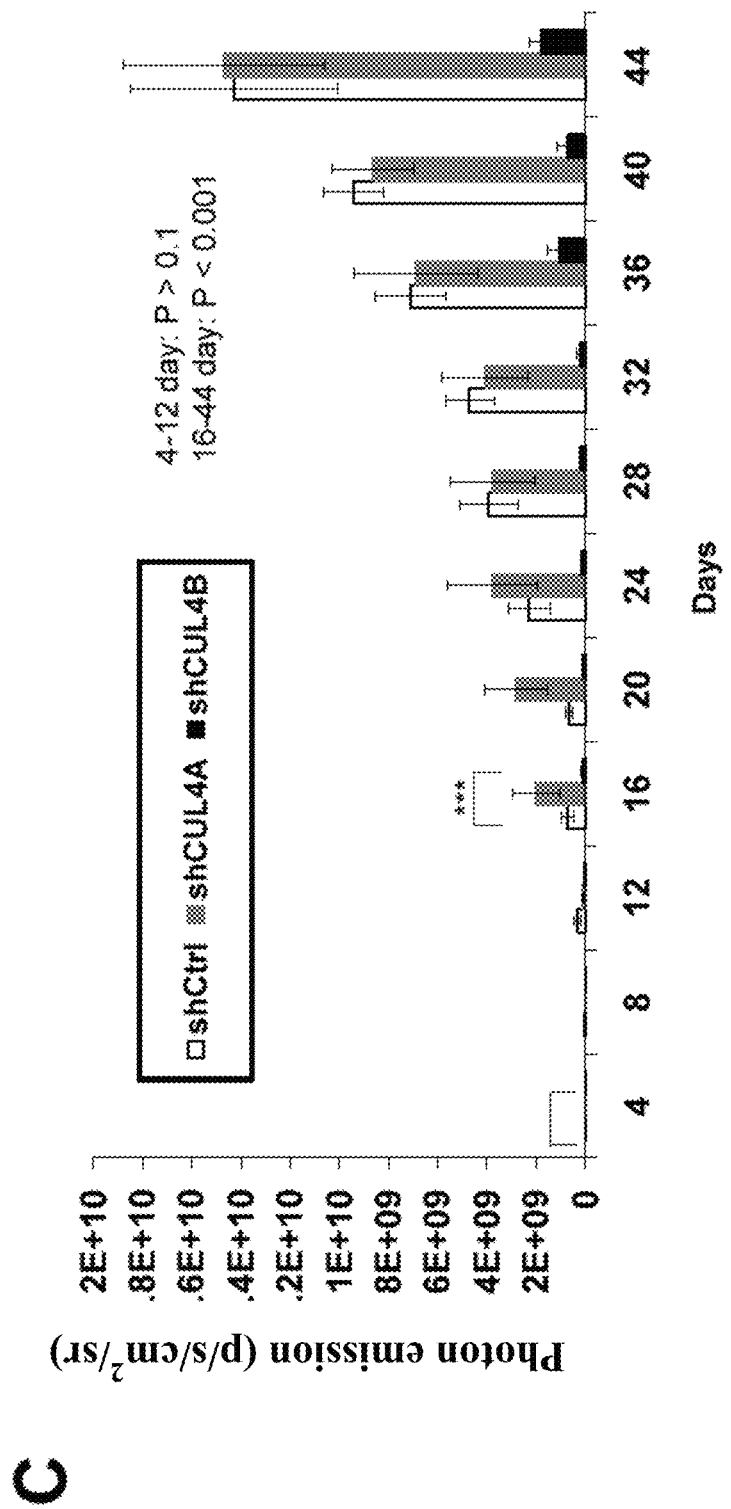
Figure 5D:
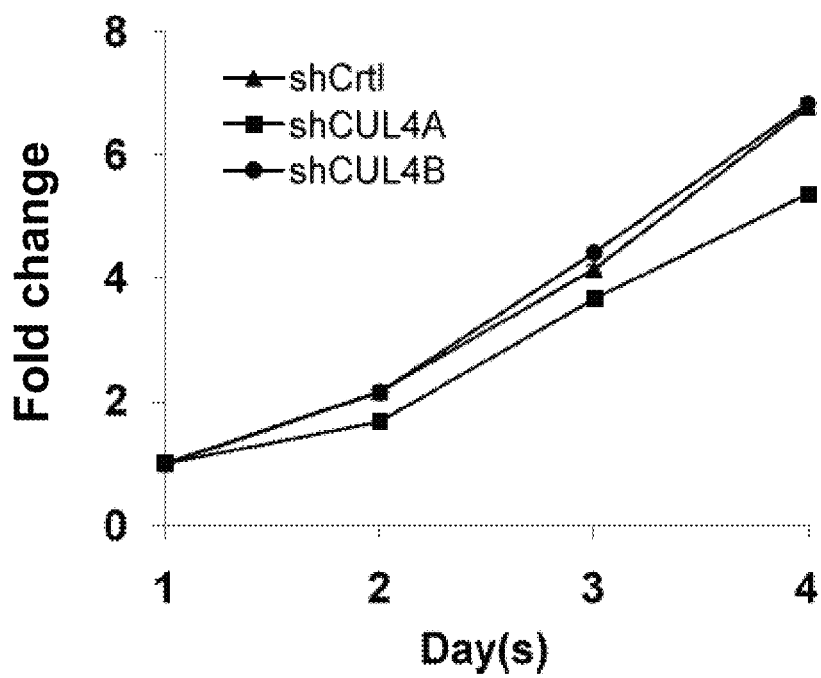
Figure 5E:
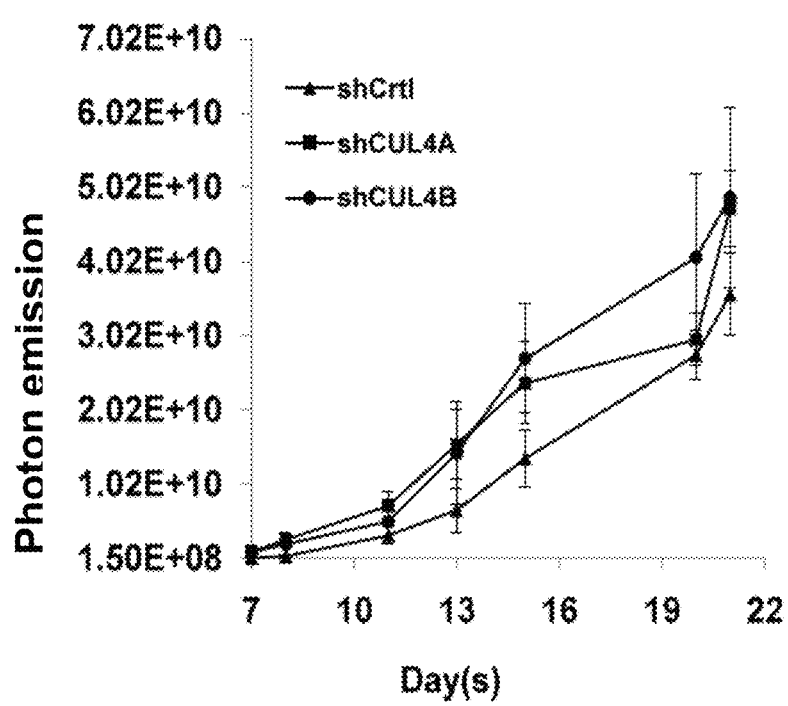
Figure 5F:
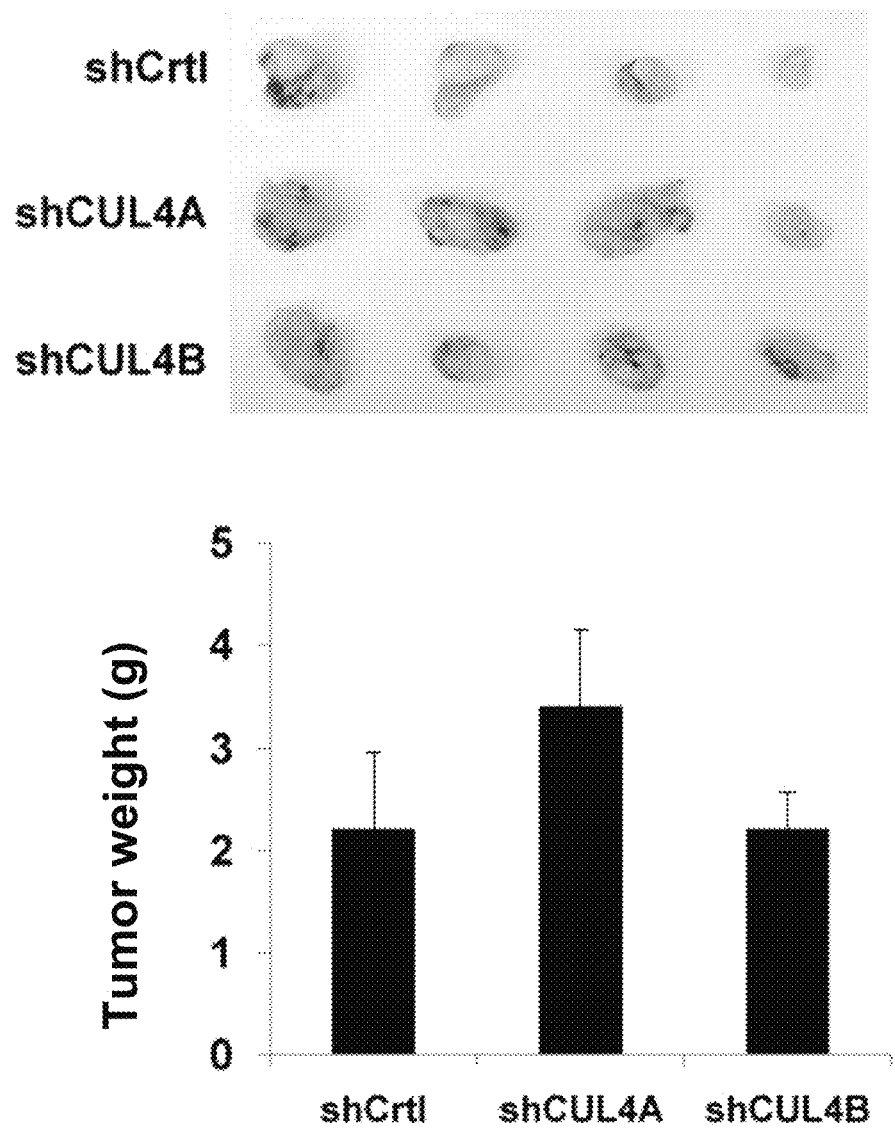

The effect of CUL4B knockdown on an organism's response to CPT treatment was tested in vivo by examining the sensitivity of BT474-CUL4B$^{k/d}$, BT474-CUL4A$^{k/d}$ and control BT474 xenograft tumors to topotecan treatment. Topotecan, (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride, is an FDA-approved Top1-directed chemotherapy for the treatment of ovarian, cervical and small cell lung cancer, under the trade name Hycamtin™. Nude mice bearing BT474 xenografts on dorsal skin were treated with topotecan every four (4) days for a period of 44 days. Prior to topotecan administration, the size of the xenograft tumors were identical (FIG. 5). Topotecan was then administered via intraperitoneal injection, and tumor mass was monitors by bioluminescent imaging in four day intervals. As shown in FIG. 5, tumors of the control and BT474-CUL4A$^{k/d}$ groups continue to grow in the presence of topotecan treatment, indicating that BT474 cells are unaffected by treatment with the Top1 inhibitor. Moreover, these data reveal that CUL4A expression has no effect on BT474 sensitivity to Top1-directed chemotherapy. Strikingly, when CUL4B was inactivated, the growth of BT474-CUL4B$^{k/d}$ xenograft tumors were largely attenuated following topotecan administration compared to the control and BT474-CUL4A$^{k/d}$ groups (p<0.001, student t test) (FIG. 5C). On the final day of treatment the size of control and shCUL4A treated xenografts were 5-fold larger in size than that of shCUL4B treated xenografts and several shCUL4B xenografts were not detectable by bioluminescent imaging (FIG. 5B). To rule out the possibility that the growth rate of xenografts were altered during the CUL4B inactivation process (treatment with shRNA) the tumor mass of the three xenograft groups were measured in the absence of topotecan treatment and the weight of the exercised xenograft tumors were analyzed. Results show that there was no significant difference in the growth rate between control, shCUL4A and shCUL4B xenografts without topotecan administration (FIG. 5E,F). Moreover, CUL4B knockdown had no effect on the growth rate of cultured BT474-CUL4B$^{k/d}$ cells in vitro, whereas CUL4A knockdown reduced the growth rate slightly (FIG. 5D). Taken together, these data show that CUL4B silencing sensitizes breast cancer cells to topotecan-mediated cytotoxicity in vivo.

Example 8. Methods and Materials

Cells.

MCF-10A and six Human breast cancer cell lines (BT474, BT20, MCF-7, MDA-MB-231, T47D and Sk-Br-3) were purchased from ATCC. MCF-10A cells were grown in mammary epithelial cell basal medium containing growth supplements (BPE, hEGF, hydrocortisone and GA-1000). BT474, BT20 and MCF-7 cells were grown in Dulbecco's modified Eagle's medium. MDA-MB-231, T47D and Sk-Br-3 cells were grown in DMEM/F12 (1:1). All media were supplemented with 10% heat inactivated fetal bovine serum, 100 units/ml penicillin, and 100 mg/ml streptomycin. All cells were cultured in at a 37° C. incubator with 5% CO2.

Drugs, Chemical and Antibodies.

Camptothecin and Topotecan were purchased from sigma. Aliquots of camptothecin were stored frozen in 12.5 mM DMSO and diluted further in DMSO or medium immediately prior to each experiment. 1 mg/ml aliquots of Topotecan were stored and frozen in sterile PBS.

Anti-CUL4B antibody (1216-1-AP) was purchased from Proteintech Group; anti-CUL4A antibody (#2699), anti-PARP antibody (#9542), anti-Caspase-3 antibody (#9662), anti-cleaved Caspase-3 antibody (#9661) and anti-MEK1/2 antibody (#4694) were purchased from Cell Signaling; anti-Top1 antibody (sc-5342) was purchased from Santa Cruz Biotechonlogy; anti-Histone H3 antibody (ab1791), anti-γH2AX (ab11174) was purchased from Abcam. The second anti-mouse, anti-rabbit or anti-goat Ig antibody conjugated with horseradish peroxidase was purchased from Amersham Biosciences.

shRNA CUL4A and CUL4B.

Two different validated shRNA CUL4A or CUL4B structures were purchased from Sigma Aldrich. One shRNA CUL4A sequence (TRCN0000006530): CCGGGCA-GAACTGATCGCAAAGCATCTCGAGATGCTTTGC-GATCAGTTCTGCTTT TT [SEQ ID NO. 4]. Another shRNA CUL4A sequence (TRCN0000320827): CCGGGT-GTGGAGAAACAGCTATTAGCTCGAGCTAATAGCT-GTTTCTCCACACTTT TTG [SEQ ID NO. 5]. One shRNA CUL4B sequence (TRCN0000006535): CCGGGCA-GAATTTAAAGAGGGTAAACTCGAGTTTACCCTCTT- TAAATTCTGCTTTT T [SEQ ID NO. 1]. Another shRNA CUL4B sequence (TRCN0000006536): CCGGGCAAT-TCTTCAGAAAGGTTTACTCGAGTAAACCTTTCT-GAAGAATTGCTTTT T [SEQ ID NO. 2]

Preparation of Total Cell Lysates.

Cells were washed twice with PBS and then lysed with buffer (10 mM HEPES pH7.9, 50 mM NaCl, 0.5M sucrose, 0.1 mM EDTA, 1% NP-40, 0.5% Triton X-100, and freshly added protease inhibitor mixtures). 5 ml Benzonase was added to the cell lysates and were rotated at 4° C. for 1.5 hours. Cellular debris was removed by centrifugation at 14000 rpm for 5 min at 4° C. The supernatant was transferred to a new container and evaluated for protein concentration (Pierce® BCA). Samples were either used immediately for assays or stored at −80° C. for subsequent analysis.

Western Blotting of Tissue Samples.

Twenty colon cancer specimens were obtained as surgical specimens and frozen. Proteins were then extracted using standard techniques and subjected to SDS-PAGE and Western blotting and detected by an anti-CUL4B antibody using γ-tubulin expression as a control. CUL4B protein expression levels were compared to that of non-cancerous control tissue (surgical margins, benign samples) samples obtained from each subject. Western blotting using a CUL4B antibody revealed that CUL4B expression was elevated in 45% (9 of 20 samples) of the cancerous tissue when compared to that of the non-cancerous control sample.

Immunoprecipitation.

Prior to extraction, cells were treated with 0.2 mM DSP (Pierce Biotechnology) at 25° C. for 30 min. 300 mg of the cellular extracts were incubated with appropriate primary antibodies or normal rabbit immunoglobin G (IgG), and rotated at 4° C. overnight or for 3 hours, followed by addition of Protein G Sepharose® 4 Fast Flow beads for four hours at 4° C. Beads were then washed four times with lysis buffer (10 mM HEPES pH7.9, 50 mM NaCl, 0.5M sucrose, 0.1 mM EDTA, 1% NP-40, 0.5% Triton X-100, and freshly added protease inhibitor mixtures). The immune complex was subjected to SDS-PAGE followed by immunoblotting with a secondary antibody. Immunodetection was performed using enhanced chemiluminescence (ECL System, Thermo Scientific) according to the manufacturer's protocol.

Fractionation of Membrane/Cytoplasmic and Nuclear Proteins.

Cells were washed twice in PBS and lysed with lysis buffer (10 mM HEPES pH7.9, 50 mM NaCl, 0.5M sucrose, 0.1 mM EDTA, 0.5% Triton X-100, and freshly added protease inhibitor mixtures) at 4° C. for 10 min. Next, cell mixtures were centrifuged at 1000 rpm for 10 min to pellet the nuclei. The supernatant was transferred to a new tube containing the cytoplasmic and membrane protein extracts. The pellet was washed twice in buffer composed of 10 mM HEPES pH7.9, 10 mM KCl, 0.1 mM EDTA, 0.1 mM EGTA, and freshly added 1 mM DTT and protease inhibitor mixtures to remove residual membrane/cytoplasmic proteins. The pellet was then incubated in buffer composed of 10 mM HEPES pH7.9, 500 mM NaCl, 0.1 mM EDTA, 0.1 mM EGTA, 0.1% NP-40 containing freshly added protease inhibitor mixtures, and then briefly sonicated to disrupt the nuclei. Lysates were then rotated at 4° C. for 2 hr. Cellular debris was removed by centrifugation at 14000 rpm for 10 min at 4° C. The supernatant was transferred to a new container, which contained nuclear proteins. Samples were evaluated for protein concentration (Pierce® BCA) and either used immediately or stored at −80° C. for further analysis.

CPT-Induced TOP1 Down Regulation Assay.

CPT-induced Top1 degradation was monitored by immunoblotting of the alkaline lysates. Briefly, for each 100-mm dish, 300 μl of 200 mM NaOH was added, and cells were then scraped with a rubber policeman. Alkaline lysates were neutralized by addition of 1 N HCl, followed by mixing with 40 μl 10× nuclease buffer (600 mM Tris-HCl pH 8.0, 50 mM $MgCl_2$, 50 mM $CaCl_2$, 5 mM dithiothreitol, 10% NP40 and freshly added protease inhibitor mixtures). Lysates were briefly sonicated (10 sec for 4 times) and benzonase Nuclease (5 ml) was used for breaking the genomic DNA and releasing Top1 from covalent Top1-DNA complexes. Lysates were then rotated at 4° C. for 2 hours and centrifuged at 14000 rpm for 5 min. The supernatant was then transferred to a new container. High salt buffer (60 mM Tris-HCl pH8.0, 500 mM NaCl, 0.1 mM EDTA, 0.1% NP40, and freshly added protease inhibitor mixtures) was added to the pellet. After rotation for 1 hour at 4° C., cellular debris was removed by centrifugation at 14000 rpm for 5 min at 4° C. The supernatant was transferred to the previous tube and total cell lysates were analyzed by SDS-gel electrophoresis and immunoblotted with anti-hTop1 antibody.

XTT Assay for Cellular Proliferation after Treatment with Camptothecin.

Synchronized cells were seeded into 96-well microplates. When cells completely attached the plate, cells were treated with the indicated concentrations of camptothecin. After 72 hours, 50 ml of XTT working solution (tetrazolium dye) was added to the each well, and then the microplate was incubated in a $CO_2$ incubator for 2 hours. The optical density was measured with a microplate reader. The survival of cells at each concentration of the drug was expressed as the percentage ratio of the optical density of cells treated with camptothecin to the optical density of the untreated cells. Measurements were performed in double triplicate. Data were expressed as the mean±S.E. Difference in the survival ratios between the two cell lines at each concentration point was assessed by the student's T test. When p value was <0.01, the difference was considered statistically significant.

Western Blot Analysis for γH2AX.

Cells in log growth phase were treated with 12.5 mM CPT for 1.5 hours, and then washed twice in PBS, scraped and incubated on ice for 20 min in hypotonic buffer (10 mM Tris-HCl, pH8.0, 1 mM KCl, 1.5 mM $MgCl_2$, 1 mM DTT, freshly added protease inhibitor mixtures). Cell lysates were centrifuged at 6000 rpm at 4° C. for 10 min. The pellets were suspended in 0.4 ml 0.4N $H_2SO_4$ at 4° C. for overnight, and centrifuged at 13000 rpm for 10 min. Histones were precipitated from the supernatant by add 0.25% volume of 100% (w/v) ice cold trichloroacetic acid. The pellets were washed once by 100% cold ethanol (−20° C.) and centrifuged again at 13000 rpm for 5 min. The pellets were dissolved in 560 ml RIPA buffer (150 mM NaCl, 50 mM HEPES, pH7.4, 0.5% Sodium Deoxycholate, 0.1% SDS, freshly added protease inhibitor mixtures) and 40 ml 10% SDS, and evaluated for protein concentration (Pierce® BCA). Samples were either used immediately for assays or stored at −80° C.

Immunocytochemistry for γH2AX.

Cells were initially grown on chamber slides. After treatment with the indicated dose of camptothecin at 37° C., cells were fixed in 4% paraformaldehyde in phosphate-buffered saline (PBS) for 10 min, washed in PBS and permeabilized in 100% methanol at −20° C. for 20 min. Cells were blocked with 10% bovine serum albumin in PBS for 1 hour, followed by incubation with 400-fold diluted rabbit anti-γH2AX antibody in PBS containing 1% bovine serum albumin at 4°

C. overnight. After three PBS washes, cells were stained with 200-fold diluted Cy3-conjugated goat anti-rabbit secondary antibody and 500-fold diluted 4',6'-diamidino-2-phenylindole (DAPI) in PBS containing 0.5% bovine serum albumin for 2 hr at room temperature. After PBS washes, cells were mounted with FluroSave™ Reagent (Calbiochem), and visualized under the fluorescence microscope, and images were captured via camera.

BrdU Incorporation Assay.

Cells in log growth phase were pulse labeled with 10 ug/ml BrdU during the last 30 min of CPT treatment. Cells were harvested by trypsinization, fixed in 70% ice-cold ethanol, and store at −20° C. Cells were incubated in 0.1N HCl-0.4 mg/ml pepsin for 30 min at room temperature to allow DNA denaturation. After pepsin was removed, cells were incubated for 10 min at 37° C. in 0.2N HCl to further denature DNA. The medium was neutralized in 0.05 M sodium borate (pH8.5), and cells were washed twice in PBS containing 0.1% bovine serum albumin. Cells were incubated for 1 hr at room temperature with an FITC-conjugated anti-BrdU antibody and treated with 1 mg/ml RNase A and 50 mg/ml propidium iodide. Samples were analysis with a flow cytometer (FACScan, BD) using the Cell Quest software (BD).

Growth of Human Breast Tumor Xenografts.

Six week old Female athymic Nu/J nude mice were purchased from Jackson Labs. Mice were housed in laminar air-flow cabinets under specific pathogen-free conditions. Nude mice were inoculated with 0.36 mg 60-day-release 17-b-estradiol pellets (Innovative Research) 24 to 48 hours before implantation of BT-474 cells. 1×10$^7$ BT-474 cells in 50 ul DMEM medium and 300 ul diluted BD Matrigel™ Basement Membrane Matrix (BD Bioscience, Matrix: PBS is 2:1) were injected subcutaneously in the right flank of each mouse. Tumors were detected once every four days by an IVIS Imaging System (Caliper Life Sciences). When tumors were available to be detected, mice were initially treated with topotecan. Topotecan was administered intraperitoneally on every fourth day from the initiation of therapy at doses of 5 mg/g.

In Vivo Bioluminescent Imaging.

The IVIS Imaging System (Caliper life sciences) was used for bioluminescent image acquisition and analysis. Ready-to-use firefly D-luciferin potassium salt in PBS (30 mg/ml) was purchased from Caliper Lifesciences. Mice were injected intraperitoneally with D-luciferin solution at 150 mg/kg. Five minutes post-injection, groups of four-five mice were placed in the specimen chamber mounted with a CCD camera, cooled to −120° C., and the images were acquired for 1-3s. The photon emission transmitted from the mice was measured and bioluminescent color images were superimposed and analyzed using the Living Image 4.0 software (Caliper life sciences). A region of interest (ROI) was manually selected over the signal intensity. Data were expressed as the mean±S.E. Difference of photon emission was assessed by the student's t test. When p value was <0.01, the difference was considered statistically significant.

Tissue Microarray.

Tissue microarrays (TMAs) were generated for 138 cases of colorectal and 185 lung cancer patient samples including 72 samples derived from subjects diagnosed with small cell lung cancer, 113 cases derived from subjects diagnosed with squamous cell carcinomas. CUL4B expression levels were measured by immunohistochemistry using a polyclonal antibody specific for CUL4B (e.g., Anti-CUL4B antibody (1216-1-AP) Proteintech Group) and not detecting the CUL4A protein. All immunostained TMAs were scored in a blinded, independent manner using the semi-quantitative scoring system, "H score" measuring the percentage and intensity of staining in a given case.

TABLE 1

| Cancer Type | Total Number of Subjects Analyzed | Number of Subjects Exhibiting Elevated CUL4B Gene Copy Number | Percent Subjects with Elevated CUL4B Expression |
|---|---|---|---|
| AML | 13 | 2 | N/A |
| Adenosquamous lung carcinoma | 4 | 3 | 75% |
| B-Cell Acute Lymphoblastic Leukemia | 10 | 5 | 50% |
| Bladder Urothelial Carcinoma | 12 | 7 | 58% |
| Blast Phase Chronic Myelogenous Leukemia | 13 | 2 | 15% |
| Brain Astrocytoma | 6 | 4 | 67% |
| Brain Glioblastoma | 22 | 10 | 45% |
| Breast Adenocarcinoma | 18 | 13 | 72% |
| Breast Carcinoma | 6 | 5 | 83% |
| Burkitt's Lymphoma | 11 | 3 | 27% |
| Colon Adenocarcinoma | 28 | 15 | 54% |
| Colon Carcinoma | 14 | 7 | 50% |
| Cutaneous Melanoma | 30 | 12 | 40% |
| Diffuse Large B-Cell Lymphoma | 15 | 6 | 40% |
| Ductal Breast Carcinoma | 10 | 9 | 90% |
| Endometrial Adenocarcinoma | 11 | 8 | 73% |
| Endometrial Endometrioid Adenocarcinoma | 10 | 8 | 80% |
| Esophageal Squamous Cell Carcinoma | 24 | 13 | 54% |
| Gastric Adenocarcinoma | 12 | 4 | 33% |
| Gastric Cancer | 17 | 7 | 41% |
| Hepatocellular Carcinoma | 24 | 13 | 54% |
| Invasive Ductal Breast Carcinoma | 18 | 12 | 66% |
| Lung Adenocarcinoma | 58 | 28 | 48% |
| Melanoma | 25 | 9 | 36% |
| Multiple Myeloma | 22 | 5 | 23% |
| Neuroblastoma | 16 | 4 | 25% |
| Ovarian Adenocarcinoma | 8 | 6 | 75% |
| Ovarian Clear Cell Adenocarcinoma | 7 | 4 | 57% |
| Pancreatic Adenocarcinoma | 21 | 10 | 48% |
| Pancreatic Carcinoma | 9 | 5 | 56% |
| Pancreatic Ductal Adenocarcinoma | 12 | 5 | 41% |
| Rhabdomyosarcoma | 7 | 5 | 71% |
| Small Cell Lung Carcinoma | 50 | 22 | 44% |
| Squamous Cell Lung Carcinoma | 23 | 14 | 60% |
| T-Cell Acute Lymphoblastic Leukemia | 15 | 4 | 27% |
| Tongue Squamous Cell Carcinoma | 16 | 4 | 25% |

What is claimed is:

1. A method of treating cancer in a subject who has been identified as expressing an elevated level of CUL4B, comprising administering to the subject an effective amount of an agent that inhibits expression or activity of CUL4B, and a Top1-directed chemotherapeutic compound, wherein inhibition of expression of CUL4B sensitizes said cancer to the Top1-directed chemotherapeutic compound, and wherein the agent is a nucleic acid comprising a nucleotide sequence selected from the group consisting of SEQ ID NO: 1, SEQ ID NO: 2, SEQ ID NO: 6 and SEQ ID NO: 7.

2. A method of sensitizing a cancer patient to a Top1-directed chemotherapeutic compound, comprising:
   obtaining a biological from a human subject;
   determining that the sample has elevated expression of CUL4B;
   administering to the subject an effective amount of an agent that inhibits expression or activity of CUL4B, wherein inhibition of expression of CUL4B sensitizes said cancer to the Top1-directed chemotherapeutic compound, and wherein the agent is a nucleic acid comprising a nucleotide sequence selected from the group consisting of SEQ ID NO: 1, SEQ ID NO: 2, SEQ ID NO: 6 and SEQ ID NO: 7.

3. The method of claim 1 or 2, wherein the Top1-directed chemotherapeutic compound is a camptothecin compound.

4. The method of claim 3, wherein the camptothecin compound is selected from the group consisting of lacto- camptothecin, topotecan, irinotecan, SN-38, rubitecan, gimatecan, karenitecin, silatecan, exatecan, lurtotecan and diflomotecan.

5. The method of claim 1 or 2, wherein the cancer is selected from the group consisting of: colorectal cancer, breast cancer, lung cancer, adenosquamous lung carcinoma, B-Cell acute lymphoblastic leukemia, bladder urothelial carcinoma, brain astrocytoma, breast adenocarcinoma, breast carcinoma, colon adenocarcinoma, colon carcinoma, ductal breast carcinoma, endometrial adenocarcinoma, endometrial endometrioid adenocarcinoma, esophageal squamous cell carcinoma, hepatocellular carcinoma, invasive ductal breast carcinoma, ovarian adenocarcinoma, rhabdomyosarcoma, squamous cell lung carcinoma, acute myeloid leukemia (AML), blast phase chronic myleogenous leukemia, brain glioblastoma, burkitts lymphoma, cutaneous melanoma, diffuse large B-cell lymphoma, gastric andenocarcinoma, gastric cancer, lung adenocarcinoma, melanoma, multiple myeloma, neuroblastoma, pancreatic adenocarcinoma, pancreatic ductal carcinoma, small cell lung carcinoma, T-cell acute lymphoblastic leukemia, and tongue squamous cell carcinoma.

6. The method of claim 1 or 2, wherein the agent is an siRNA or shRNA.

7. The method of claim 1, wherein the agent comprises SEQ ID NO: 6.

8. The method of claim 1, wherein the agent comprises SEQ ID NO: 1.

9. The method of claim 1, wherein the agent comprises SEQ ID NO. 2.

10. The method of claim 1, wherein the agent comprises SEQ ID NO: 7.

11. The method of claim 2, wherein the agent comprises SEQ ID NO: 6.

12. The method of claim 2, wherein the agent comprises SEQ ID NO: 7.

13. The method of claim 2, wherein the agent comprises SEQ ID NO: 1.

14. The method of claim 2, wherein the agent comprises SEQ ID NO: 2.

\* \* \* \* \*

SEQUENCE LISTING

<160> NUMBER OF SEQ ID NOS: 8

<210> SEQ ID NO 1
<211> LENGTH: 57
<212> TYPE: DNA
<213> ORGANISM: Artificial Sequence
<220> FEATURE:
<223> OTHER INFORMATION: Encoding short hairpin RNA targeting CUL4B
      transcript

<400> SEQUENCE: 1
ccgggcagaa tttaaagagg gtaaactcga gtttaccctc tttaaattct gctttttt    57

<210> SEQ ID NO 2
<211> LENGTH: 57
<212> TYPE: DNA
<213> ORGANISM: Artificial Sequence
<220> FEATURE:
<223> OTHER INFORMATION: Encoding short hairpin RNA targeting CUL4B
      transcript

<400> SEQUENCE: 2
ccgggcaatt cttcagaaag gtttactcga gtaaaccttt ctgaagaatt gctttttt    57

<210> SEQ ID NO 3
<211> LENGTH: 913
<212> TYPE: PRT
<213> ORGANISM: Homo sapiens

<400> SEQUENCE: 3

Met Met Ser Gln Ser Ser Gly Ser Gly Asp Gly Asn Asp Asp Glu Ala
1               5                   10                  15

Thr Thr Ser Lys Asp Gly Gly Phe Ser Ser Pro Ser Pro Ser Ala Ala
            20                  25                  30

Ala Ala Ala Gln Glu Val Arg Ser Ala Thr Asp Gly Asn Thr Ser Thr
        35                  40                  45

Thr Pro Pro Thr Ser Ala Lys Lys Arg Lys Leu Asn Ser Ser Ser Ser
    50                  55                  60

Ser Ser Ser Asn Ser Ser Asn Glu Arg Glu Asp Phe Asp Ser Thr Ser
65                  70                  75                  80

Ser Ser Ser Ser Thr Pro Pro Leu Gln Pro Arg Asp Ser Ala Ser Pro
                85                  90                  95

Ser Thr Ser Ser Phe Cys Leu Gly Val Ser Val Ala Ala Ser Ser His
            100                 105                 110

Val Pro Ile Gln Lys Lys Leu Arg Phe Glu Asp Thr Leu Glu Phe Val
        115                 120                 125

Gly Phe Asp Ala Lys Met Ala Glu Glu Ser Ser Ser Ser Ser Ser Ser
    130                 135                 140

Ser Ser Pro Thr Ala Ala Thr Ser Gln Gln Gln Gln Leu Lys Asn Lys
145                 150                 155                 160

Ser Ile Leu Ile Ser Ser Val Ala Ser Val His His Ala Asn Gly Leu
                165                 170                 175

Ala Lys Ser Ser Thr Thr Val Ser Ser Phe Ala Asn Ser Lys Pro Gly
            180                 185                 190

Ser Ala Lys Lys Leu Val Ile Lys Asn Phe Lys Asp Lys Pro Lys Leu
        195                 200                 205

Pro Glu Asn Tyr Thr Asp Glu Thr Trp Gln Lys Leu Lys Glu Ala Val
    210                 215                 220

-continued

```
Glu Ala Ile Gln Asn Ser Thr Ser Ile Lys Tyr Asn Leu Glu Glu Leu
225                 230                 235                 240

Tyr Gln Ala Val Glu Asn Leu Cys Ser Tyr Lys Ile Ser Ala Asn Leu
                245                 250                 255

Tyr Lys Gln Leu Arg Gln Ile Cys Glu Asp His Ile Lys Ala Gln Ile
            260                 265                 270

His Gln Phe Arg Glu Asp Ser Leu Asp Ser Val Leu Phe Leu Lys Lys
        275                 280                 285

Ile Asp Arg Cys Trp Gln Asn His Cys Arg Gln Met Ile Met Ile Arg
    290                 295                 300

Ser Ile Phe Leu Phe Leu Asp Arg Thr Tyr Val Leu Gln Asn Ser Met
305                 310                 315                 320

Leu Pro Ser Ile Trp Asp Met Gly Leu Glu Leu Phe Arg Ala His Ile
                325                 330                 335

Ile Ser Asp Gln Lys Val Gln Asn Lys Thr Ile Asp Gly Ile Leu Leu
            340                 345                 350

Leu Ile Glu Arg Glu Arg Asn Gly Glu Ala Ile Asp Arg Ser Leu Leu
        355                 360                 365

Arg Ser Leu Leu Ser Met Leu Ser Asp Leu Gln Ile Tyr Gln Asp Ser
    370                 375                 380

Phe Glu Gln Arg Phe Leu Glu Glu Thr Asn Arg Leu Tyr Ala Ala Glu
385                 390                 395                 400

Gly Gln Lys Leu Met Gln Glu Arg Glu Val Pro Glu Tyr Leu His His
                405                 410                 415

Val Asn Lys Arg Leu Glu Glu Ala Asp Arg Leu Ile Thr Tyr Leu
            420                 425                 430

Asp Gln Thr Thr Gln Lys Ser Leu Ile Ala Thr Val Glu Lys Gln Leu
        435                 440                 445

Leu Gly Glu His Leu Thr Ala Ile Leu Gln Lys Gly Leu Asn Asn Leu
    450                 455                 460

Leu Asp Glu Asn Arg Ile Gln Asp Leu Ser Leu Leu Tyr Gln Leu Phe
465                 470                 475                 480

Ser Arg Val Arg Gly Gly Val Gln Val Leu Leu Gln Gln Trp Ile Glu
                485                 490                 495

Tyr Ile Lys Ala Phe Gly Ser Thr Ile Val Ile Asn Pro Glu Lys Asp
            500                 505                 510

Lys Thr Met Val Gln Glu Leu Leu Asp Phe Lys Asp Lys Val Asp His
        515                 520                 525

Ile Ile Asp Ile Cys Phe Leu Lys Asn Glu Lys Phe Ile Asn Ala Met
    530                 535                 540

Lys Glu Ala Phe Glu Thr Phe Ile Asn Lys Arg Pro Asn Lys Pro Ala
545                 550                 555                 560

Glu Leu Ile Ala Lys Tyr Val Asp Ser Lys Leu Arg Ala Gly Asn Lys
                565                 570                 575

Glu Ala Thr Asp Glu Glu Leu Glu Lys Met Leu Asp Lys Ile Met Ile
            580                 585                 590

Ile Phe Arg Phe Ile Tyr Gly Lys Asp Val Phe Glu Ala Phe Tyr Lys
        595                 600                 605

Lys Asp Leu Ala Lys Arg Leu Leu Val Gly Lys Ser Ala Ser Val Asp
    610                 615                 620

Ala Glu Lys Ser Met Leu Ser Lys Leu Lys His Glu Cys Gly Ala Ala
625                 630                 635                 640
```

-continued

```
Phe Thr Ser Lys Leu Glu Gly Met Phe Lys Asp Met Glu Leu Ser Lys
                645                 650                 655

Asp Ile Met Ile Gln Phe Lys Gln Tyr Met Gln Asn Gln Asn Val Pro
            660                 665                 670

Gly Asn Ile Glu Leu Thr Val Asn Ile Leu Thr Met Gly Tyr Trp Pro
        675                 680                 685

Thr Tyr Val Pro Met Glu Val His Leu Pro Pro Glu Met Val Lys Leu
    690                 695                 700

Gln Glu Ile Phe Lys Thr Phe Tyr Leu Gly Lys His Ser Gly Arg Lys
705                 710                 715                 720

Leu Gln Trp Gln Ser Thr Leu Gly His Cys Val Leu Lys Ala Glu Phe
                725                 730                 735

Lys Glu Gly Lys Lys Glu Leu Gln Val Ser Leu Phe Gln Thr Leu Val
            740                 745                 750

Leu Leu Met Phe Asn Glu Gly Glu Phe Ser Leu Glu Glu Ile Lys
        755                 760                 765

Gln Ala Thr Gly Ile Glu Asp Gly Glu Leu Arg Arg Thr Leu Gln Ser
    770                 775                 780

Leu Ala Cys Gly Lys Ala Arg Val Leu Ala Lys Asn Pro Lys Gly Lys
785                 790                 795                 800

Asp Ile Glu Asp Gly Asp Lys Phe Ile Cys Asn Asp Phe Lys His
                805                 810                 815

Lys Leu Phe Arg Ile Lys Ile Asn Gln Ile Gln Met Lys Glu Thr Val
            820                 825                 830

Glu Glu Gln Ala Ser Thr Thr Glu Arg Val Phe Gln Asp Arg Gln Tyr
        835                 840                 845

Gln Ile Asp Ala Ala Ile Val Arg Ile Met Lys Met Arg Lys Thr Leu
    850                 855                 860

Ser His Asn Leu Leu Val Ser Glu Val Tyr Asn Gln Leu Lys Phe Pro
865                 870                 875                 880

Val Lys Pro Ala Asp Leu Lys Lys Arg Ile Glu Ser Leu Ile Asp Arg
                885                 890                 895

Asp Tyr Met Glu Arg Asp Lys Glu Asn Pro Asn Gln Tyr Asn Tyr Ile
            900                 905                 910

Ala
```

<210> SEQ ID NO 4
<211> LENGTH: 57
<212> TYPE: DNA
<213> ORGANISM: Artificial Sequence
<220> FEATURE:
<223> OTHER INFORMATION: Encoding short hairpin RNA targeting CUL4A gene
      transcript

<400> SEQUENCE: 4
ccgggcagaa ctgatcgcaa agcatctcga gatgctttgc gatcagttct gctttttt        57

<210> SEQ ID NO 5
<211> LENGTH: 58
<212> TYPE: DNA
<213> ORGANISM: Artificial Sequence
<220> FEATURE:
<223> OTHER INFORMATION: Encoding short hairpin RNA targeting CUL4A gene
      transcript

<400> SEQUENCE: 5
ccgggtgtgg agaaacagct attagctcga gctaatagct gtttctccac acttttttg        58

<210> SEQ ID NO 6
<211> LENGTH: 21
<212> TYPE: DNA
<213> ORGANISM: Artificial Sequence
<220> FEATURE:
<223> OTHER INFORMATION: Encoding a shRNA targeting sequence for CUL4B
      inhibition

<400> SEQUENCE: 6
tttaccctct ttaaattctg c                                              21

<210> SEQ ID NO 7
<211> LENGTH: 21
<212> TYPE: DNA
<213> ORGANISM: Artificial Sequence
<220> FEATURE:
<223> OTHER INFORMATION: Encoding a shRNA targeting sequence for CUL4B
      inhibition

<400> SEQUENCE: 7
taaacctttc tgaagaattg c                                              21

<210> SEQ ID NO 8
<211> LENGTH: 895
<212> TYPE: PRT
<213> ORGANISM: Homo sapiens

<400> SEQUENCE: 8

Met Phe Pro Thr Gly Phe Ser Ser Pro Ser Pro Ser Ala Ala Ala
1               5                   10                  15

Ala Gln Glu Val Arg Ser Ala Thr Asp Gly Asn Thr Ser Thr Thr Pro
            20                  25                  30

Pro Thr Ser Ala Lys Lys Arg Lys Leu Asn Ser Ser Ser Ser Ser Ser
        35                  40                  45

Ser Asn Ser Ser Asn Glu Arg Glu Asp Phe Asp Ser Thr Ser Ser Ser
    50                  55                  60

Ser Ser Thr Pro Pro Leu Gln Pro Arg Asp Ser Ala Ser Pro Ser Thr
65                  70                  75                  80

Ser Ser Phe Cys Leu Gly Val Ser Val Ala Ala Ser Ser His Val Pro
                85                  90                  95

Ile Gln Lys Lys Leu Arg Phe Glu Asp Thr Leu Glu Phe Val Gly Phe
            100                 105                 110

Asp Ala Lys Met Ala Glu Glu Ser Ser Ser Ser Ser Ser Ser Ser Ser
        115                 120                 125

Pro Thr Ala Ala Thr Ser Gln Gln Gln Gln Leu Lys Asn Lys Ser Ile
    130                 135                 140

Leu Ile Ser Ser Val Ala Ser Val His His Ala Asn Gly Leu Ala Lys
145                 150                 155                 160

Ser Ser Thr Thr Val Ser Ser Phe Ala Asn Ser Lys Pro Gly Ser Ala
                165                 170                 175

Lys Lys Leu Val Ile Lys Asn Phe Lys Asp Lys Pro Lys Leu Pro Glu
            180                 185                 190

Asn Tyr Thr Asp Glu Thr Trp Gln Lys Leu Lys Glu Ala Val Glu Ala
        195                 200                 205

Ile Gln Asn Ser Thr Ser Ile Lys Tyr Asn Leu Glu Glu Leu Tyr Gln
    210                 215                 220

Ala Val Glu Asn Leu Cys Ser Tyr Lys Ile Ser Ala Asn Leu Tyr Lys
225                 230                 235                 240

-continued

```
Gln Leu Arg Gln Ile Cys Glu Asp His Ile Lys Ala Gln Ile His Gln
            245                 250                 255

Phe Arg Glu Asp Ser Leu Asp Ser Val Leu Phe Leu Lys Lys Ile Asp
        260                 265                 270

Arg Cys Trp Gln Asn His Cys Arg Gln Met Ile Met Ile Arg Ser Ile
        275                 280                 285

Phe Leu Phe Leu Asp Arg Thr Tyr Val Leu Gln Asn Ser Met Leu Pro
290                 295                 300

Ser Ile Trp Asp Met Gly Leu Glu Leu Phe Ala His Ile Ile Ser
305                 310                 315                 320

Asp Gln Lys Val Gln Asn Lys Thr Ile Asp Gly Ile Leu Leu Ile
            325                 330                 335

Glu Arg Glu Arg Asn Gly Glu Ala Ile Asp Arg Ser Leu Leu Arg Ser
            340                 345                 350

Leu Leu Ser Met Leu Ser Asp Leu Gln Ile Tyr Gln Asp Ser Phe Glu
            355                 360                 365

Gln Arg Phe Leu Glu Glu Thr Asn Arg Leu Tyr Ala Ala Glu Gly Gln
            370                 375                 380

Lys Leu Met Gln Glu Arg Glu Val Pro Glu Tyr Leu His His Val Asn
385                 390                 395                 400

Lys Arg Leu Glu Glu Glu Ala Asp Arg Leu Ile Thr Tyr Leu Asp Gln
            405                 410                 415

Thr Thr Gln Lys Ser Leu Ile Ala Thr Val Glu Lys Gln Leu Leu Gly
            420                 425                 430

Glu His Leu Thr Ala Ile Leu Gln Lys Gly Leu Asn Asn Leu Leu Asp
            435                 440                 445

Glu Asn Arg Ile Gln Asp Leu Ser Leu Leu Tyr Gln Leu Phe Ser Arg
        450                 455                 460

Val Arg Gly Gly Val Gln Val Leu Leu Gln Gln Trp Ile Glu Tyr Ile
465                 470                 475                 480

Lys Ala Phe Gly Ser Thr Ile Val Ile Asn Pro Glu Lys Asp Lys Thr
            485                 490                 495

Met Val Gln Glu Leu Leu Asp Phe Lys Asp Lys Val Asp His Ile Ile
            500                 505                 510

Asp Ile Cys Phe Leu Lys Asn Glu Lys Phe Ile Asn Ala Met Lys Glu
        515                 520                 525

Ala Phe Glu Thr Phe Ile Asn Lys Arg Pro Asn Lys Pro Ala Glu Leu
            530                 535                 540

Ile Ala Lys Tyr Val Asp Ser Lys Leu Arg Ala Gly Asn Lys Glu Ala
545                 550                 555                 560

Thr Asp Glu Glu Leu Glu Lys Met Leu Asp Lys Ile Met Ile Ile Phe
            565                 570                 575

Arg Phe Ile Tyr Gly Lys Asp Val Phe Glu Ala Phe Tyr Lys Lys Asp
            580                 585                 590

Leu Ala Lys Arg Leu Leu Val Gly Lys Ser Ala Ser Val Asp Ala Glu
            595                 600                 605

Lys Ser Met Leu Ser Lys Leu Lys His Glu Cys Gly Ala Ala Phe Thr
610                 615                 620

Ser Lys Leu Glu Gly Met Phe Lys Asp Met Glu Leu Ser Lys Asp Ile
625                 630                 635                 640

Met Ile Gln Phe Lys Gln Tyr Met Gln Asn Gln Asn Val Pro Gly Asn
            645                 650                 655
```

-continued

```
Ile Glu Leu Thr Val Asn Ile Leu Thr Met Gly Tyr Trp Pro Thr Tyr
            660                 665             670

Val Pro Met Glu Val His Leu Pro Pro Glu Met Val Lys Leu Gln Glu
        675             680             685

Ile Phe Lys Thr Phe Tyr Leu Gly Lys His Ser Gly Arg Lys Leu Gln
        690             695             700

Trp Gln Ser Thr Leu Gly His Cys Val Leu Lys Ala Glu Phe Lys Glu
705                 710             715                 720

Gly Lys Lys Glu Leu Gln Val Ser Leu Phe Gln Thr Leu Val Leu Leu
                725             730                 735

Met Phe Asn Glu Gly Glu Glu Phe Ser Leu Glu Glu Ile Lys Gln Ala
            740             745             750

Thr Gly Ile Glu Asp Gly Glu Leu Arg Arg Thr Leu Gln Ser Leu Ala
            755             760             765

Cys Gly Lys Ala Arg Val Leu Ala Lys Asn Pro Lys Gly Lys Asp Ile
    770             775             780

Glu Asp Gly Asp Lys Phe Ile Cys Asn Asp Asp Phe Lys His Lys Leu
785             790             795                 800

Phe Arg Ile Lys Ile Asn Gln Ile Gln Met Lys Glu Thr Val Glu Glu
                805             810             815

Gln Ala Ser Thr Thr Glu Arg Val Phe Gln Asp Arg Gln Tyr Gln Ile
            820             825             830

Asp Ala Ala Ile Val Arg Ile Met Lys Met Arg Lys Thr Leu Ser His
            835             840             845

Asn Leu Leu Val Ser Glu Val Tyr Asn Gln Leu Lys Phe Pro Val Lys
850                 855             860

Pro Ala Asp Leu Lys Lys Arg Ile Glu Ser Leu Ile Asp Arg Asp Tyr
865             870             875             880

Met Glu Arg Asp Lys Glu Asn Pro Asn Gln Tyr Asn Tyr Ile Ala
                885             890             895
```